US006544789B1

(12) United States Patent
Raskin et al.

(10) Patent No.: US 6,544,789 B1
(45) Date of Patent: Apr. 8, 2003

(54) PHOSPHORUS-CONTROLLABLE RECOMBINANT EXPRESSION OF POLYPEPTIDES IN PLANTS

(75) Inventors: Ilya Raskin, Manalapan, NJ (US); Shoshan Haran, Kibbutz Be'eri (IL)

(73) Assignee: Board of Trustees, Rutgers, The State University of New Jersey, New Brunswick, NJ (US)

(*) Notice: Subject to any disclaimer, the term of this patent is extended or adjusted under 35 U.S.C. 154(b) by 0 days.

(21) Appl. No.: 09/523,899

(22) Filed: Mar. 13, 2000

(51) Int. Cl.$^7$ .......................... A01H 3/00; C07H 21/04; C12N 5/14
(52) U.S. Cl. .................. 435/419; 435/410; 435/320.1; 435/252.3; 436/24.1; 436/23.6; 800/278; 800/295
(58) Field of Search ................................. 435/468, 470, 435/472, 476, 410, 419, 320.1, 420, 252.3; 536/24.1, 23.6; 800/278, 295

(56) References Cited

U.S. PATENT DOCUMENTS

| 5,580,768 A | 12/1996 | Boffey et al. ............ 435/172.3 |
| 5,650,307 A | 7/1997 | Sijmons et al. .......... 435/172.3 |

FOREIGN PATENT DOCUMENTS

| EP | A-0 243 553 | 11/1987 |
| WO | WO 84/02920 | 8/1984 |
| WO | WO 96/04392 | 2/1996 |

OTHER PUBLICATIONS

Chunming Liu et al., Tomato Phosphate Transporter Genes Are Differentially Regulated in Plant Tissues by Phosphorus 1, Plant Physiol, (1998) 116, pp. 91–99.*
The cloning of two Arabidopsis genes belonging to a phosphate transporter family, The Plant Journal (1997), 11 (1) pp. 83–92.*
Xiaoying Lin et al., Sequence and analysis of chromosome 2 of the plant *Arabidopsis thaliana*, Nature, vol. 402, Dec. 16, 1999, pp. 761–768.*
Abdulaev, et al., "Functional Expression of Bovine Opsin in the Methylotrophic Yeast *Pichia pastoris,*" *Protein Exp. & Purif.* 10:61–69 (1997).
Braspenning, et al., "Secretion of Heterologous Proteins from *Schizosaccharomyces pombe* Using the Homologous Leader Sequence of pho1+ Acid Phosphatase," *Biochem. Biophys. Res. Commun.* 245:166–171 (1998).
Carswell, et al., "Disruption of the phosphate–starvation response of oilseed rape suspension cells by the fungicide phosphonate," *Planta* 203:67–74 (1997).
Christou, "Strategies for variety–independent genetic transformation of important cereals, legumes and woody species utilizing particle bombardment," *Euphytica* 85:13–27 (1995).

Duff, et al., "The role of acid phosphatases in plant phosphorus metabolism," *Physiol. Plantarum* 90:791–800 (1994).
Ferminan et al., "The KIPHO5 gene encoding a repressible acid phosphatase in the yeast *Kluyveromyces lactis:* cloning, sequencing and transcriptional analysis of the gene, and purification and properties of the enzyme," *Microbiol.* 143:2615–2625 (1997).
Ferminan, et al., "Heterologous Protein Secretion Directed by a Repressible Acid Phosphatase System of *Kluyveromyces lactis:* Characterization of Upstream Region–Activating Sequences in the KIPHO5 Gene," *Appl. Environ. Microbiol.* 64:2403–2408 (1998).
Genbank Acc. No. U48448.
Genback Acc. No. Z71395.
Herbers, et al., "A Thermostable Xylanase from *Clostridium thermocellum* Expressed at High Levels in the Apoplast of Transgenic Tobacco Has No Detrimental Effects and Is Easily Purified," *Bio/Technology* 13:63–66 (1995).
Jahne, et al., "Genetic engineering of cereal crop plants: a review," *Euphytica* 85:35–44 (1995).
Kai, et al., "Effective production of recombinant protein by using inducible pho promoter," *Seibutsu–kogaku* 71:317–323 (1993).
MacRae, et al., "Heterologous protein secretion directed by a repressible acid phosphatase system of *Aspergillus niger,*" *Gene* 132:193–198 (1993).
Mehta, et al., "Hepatitis B virus (HBV) envelope glycoproteins vary drastically in their sensitivity to glycan processing: Evidence that alteration of a single N–linked glycosylation site can regulate HBV secretion," *Proc. Natl. Acad. Sci.* (USA) 94:1822–1827 (1997).
Patel, et al., "A Secreted Purple Acid Phosphatase from Arabidopsis," *Plant Physiol.* 111 (2 Supp.):81 (1996).

(List continued on next page.)

*Primary Examiner*—Phuong T. Bui
(74) *Attorney, Agent, or Firm*—Marshall, Gerstein & Borun

(57) ABSTRACT

Materials and methods relating to the use of phosphorus-controllable plant promoters to express operably linked polynucleotides in plant cells, intact plant portions or whole plants, and the optional recovery of the expressed polypeptides, are disclosed. The materials of the invention are the recombinant expression units including a phosphorus-controllable plant promoter and an operably linked, non-native, polynucleotide coding region. The methods of the invention use plant materials that are intact, living and capable of secreting (plant cells) or exuding (intact plant portions and whole plants) the expressed polypeptides. The methods of the invention minimize operator intervention and exploit solar energy and the minimal nutrient needs of photoautotrophic organisms to provide inexpensive and indefinitely sustainable methods for controllably producing a variety of coding region products.

26 Claims, 6 Drawing Sheets

OTHER PUBLICATIONS

Figure 1:
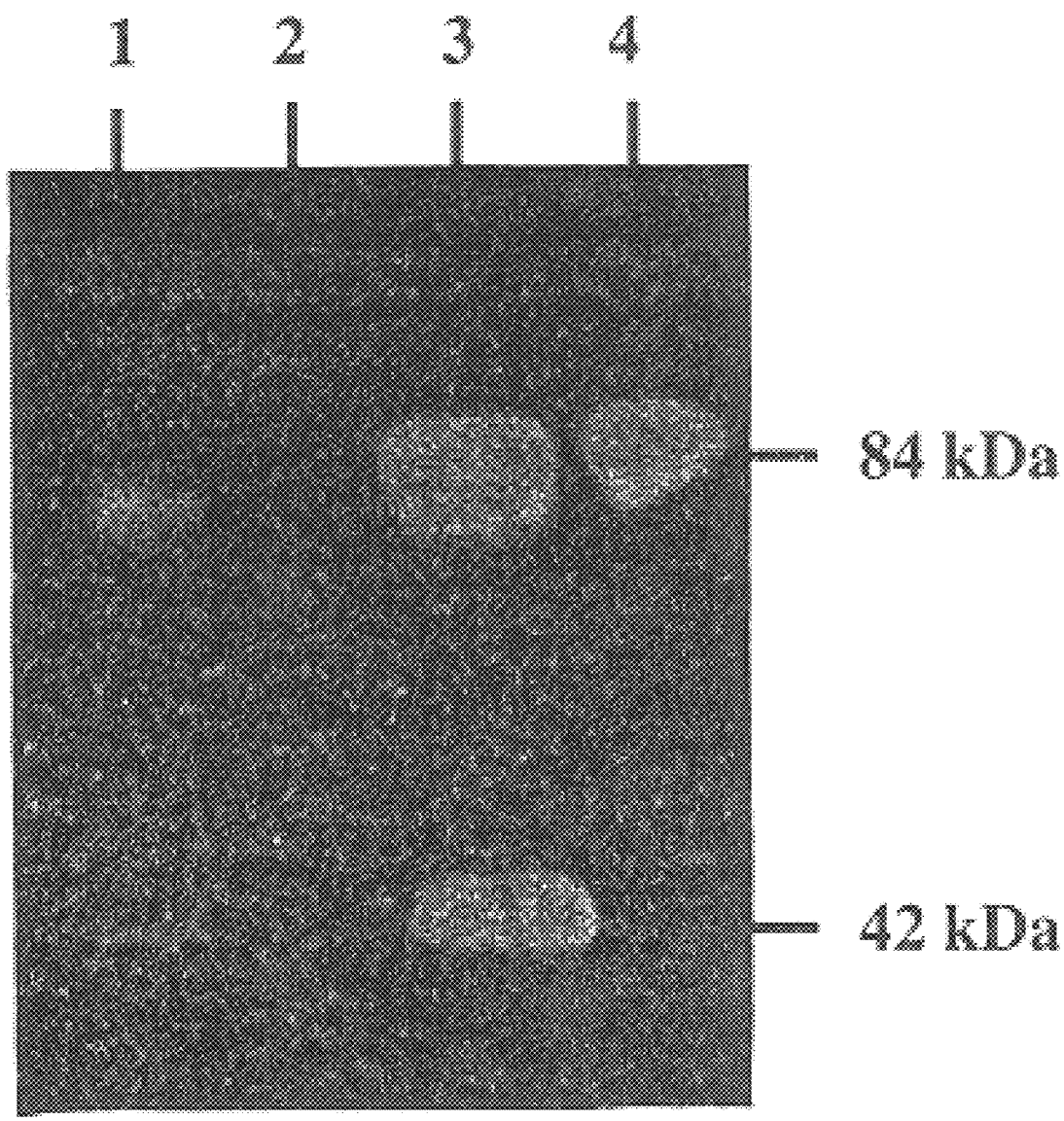

Phongdara, et al., "Cloning and characterization of the gene encoding a repressible acid phosphatase (PH01) from the methylotophic yeast *Hansenula polymorpha*," *Appl. Microbiol. Biotechnol.* 50:77–84 (1998).

Shigematsu, et al., "Expression of Human Soluble Tissue Factor in Yeast and Enzymatic Properties of Its Complex with Factor VIIa*," *J. Biol. Chem.* 267:21329–21337 (1992).

Smith, et al., "*Agrobacterium tumefaciens* Transformation of Monocotyledons," *Crop Science* 35:301–309 (1995).

Trull, et al., "Analysis of the Response to Low Phosphorus in *Arabidopsis*," *Plant Physiol.* 105 (1 Supp): 112 (1994).

Trull, et al., "The responses of wild–type and ABA mutant *Arabidopsis thaliana* plants to phosphorus starvation," *Plant, Cell and Environ.* 20:85–92 (1997).

Williamson, et al., "Acid Phosphatase–1 from Nematode Resistant Tomato Isolation and Characterization of its Gene," *Plant Physiol.* 97:139–146 (1991).

Wongsamuth, et al., "Production of Monoclonal Antibodies by Tobacco Hairy Roots," *Biotech, and Bioengineer*, 54:401–415 (1997).

* cited by examiner

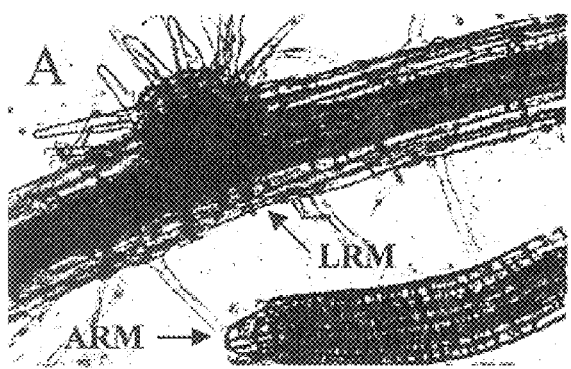
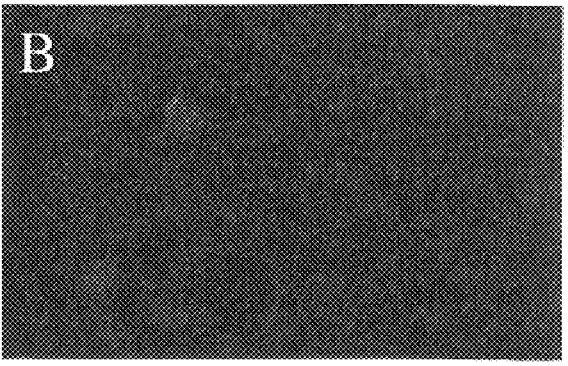
FIG. 5A  FIG. 5B
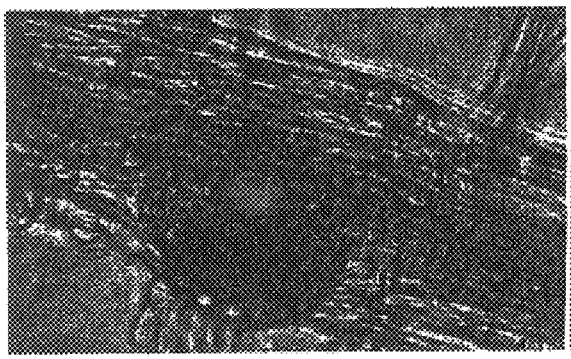
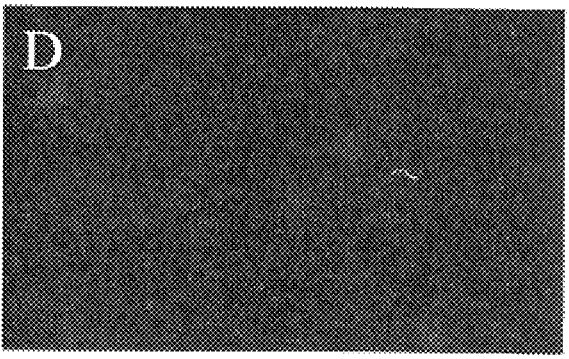
FIG. 5C  FIG. 5D
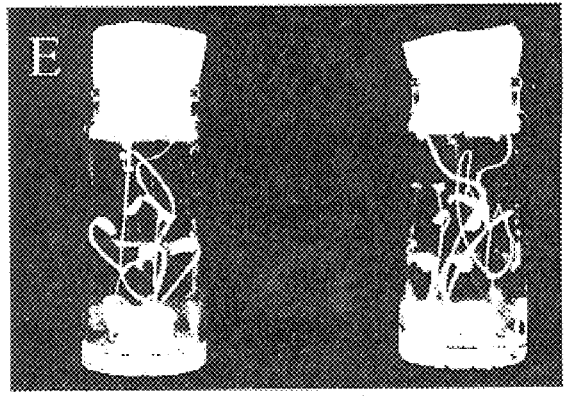
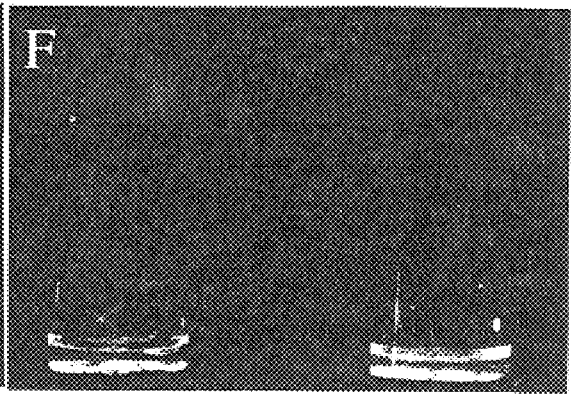
FIG. 5E  FIG. 5F

```
                        SEQUENCE LISTING

<160> NUMBER OF SEQ ID NOS: 13

<210> SEQ ID NO 1
<211> LENGTH: 1274
<212> TYPE: DNA
<213> ORGANISM: A. thaliana
<220> FEATURE:
<223> OTHER INFORMATION: A. thaliana acid phosphatase promoter region

<400> SEQUENCE: 1
gctgcctgca ggtcgacggc ccgggctggt aacgaaaatt taaatatact aaatataaac        60
atcattgaaa ttatatatta ttgatatacc ttacatatat ttgggaaagt ttataaaata      120
tgtaaaagaa aaagggtttt ataaccggat tatatctaac cgaattatgt taaatatcta      180
```

-continued

```
accgaattat gttaaatttt ataatagcct aactagagac tggaagcaat gatatcgagc      240
ttaaaggagt gctattgatt tataaattta tatagaattt gaaaatcttt attaattata      300
aaattaaaat atatgaattt taaaataata tgtgtttatc ccatggattt gaatccttct      360
attttctctt tcaaatccat ttaattttat ttaaaacata atttggattc tcaaatccaa      420
aaacaaatga ctaaacgaat aacaaaggat tttaactagt atttataaat cattgaatca      480
ataacacatg atattaatta aaattttaaa atcaataatt aaattacaaa tgattttttgt     540 tcggattttc aattcattat aaatctataa accaataacc cttcctaaac aaaaaggtaa      600
tgaaaatata tttttaaaaa aagcttattt tacattcaaa atcttgttttt aaaatctgta     660 agaaaaaaat gaaagcaaca ctatcaattg tttcctacaa cacttttttaa tcgatattaa     720 aaaaaaaaaa aagatagtta gagcattttc attggaagta tctcaatgag atacccaaca      780
aaaaaaaaat atgagaggaa ggagaaaaaa taggagagaa ggagagatga gtttctcttc      840
cgagaaactt tgagaaacta ttctcatcca atttggacaa atgtcatcat actattagtt      900
caattattaa ataataatta atatatttgt tttagttaaa atattaatat atattttttt      960
tagaaacttt tcttgttttt agatagagat ggtcttagaa gccttcattt tcaaaggttg     1020
attaaaaata aaataaaaat ttggaatatc cacttgcgat cctttcttgg aaaaaaaaa     1080 aaaaatcata tgattgtgtc tggccagaca agctagctat ctcatttaat ttcccaaaaa     1140
gaaaatataa acgttcttcg tctcggattc agagaaacta atcttgagga tgagttcaag     1200
atctgacctc aaaatcaaac gagtttcttt gataatcccc ctgctaagtg ttcttgttga     1260
gttttgctat ggag                                                       1274
```

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: primer
<223> OTHER INFORMATION: Forward Clamp1b

<400> SEQUENCE: 2

```
ggttcgaatt cgatctcaca acagtgggca tgg                                    33
```

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: primer
<223> OTHER INFORMATION: Reverse Clamprev

<400> SEQUENCE: 3

```
ctctttaaac catggagacc tcagcggaga cgac                                   34
```

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: synthetic
<223> OTHER INFORMATION: signal peptide

<400> SEQUENCE: 4

```
Met Leu Leu Leu Leu Leu Leu Leu Gly Leu Arg Leu Gln Leu Ser Leu
 1               5                  10                  15

Gly
```

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: primer
<223> OTHER INFORMATION: Upper primer 568U

<400> SEQUENCE: 5
ttgttgagtt ttgctatgga g                                    21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: primer
<223> OTHER INFORMATION: Upper primer 608U

<400> SEQUENCE: 6
cagaggaagt gatttaccag a                                    21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: primer
<223> OTHER INFORMATION: Lower primer 1383L

<400> SEQUENCE: 7
tatcccatct attgttgtcg t                                    21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: primer
<223> OTHER INFORMATION: Lower primer 1561L

<400> SEQUENCE: 8
acgccctttt gatggaatac c                                    21

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: primer
<223> OTHER INFORMATION: Primer specific for A. thaliana acid
      phosphatase: GSP1

<400> SEQUENCE: 9
tgtcatctgg taaatcactt cctct                                25

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence: primer
<223> OTHER INFORMATION: Primer specific for A. thaliana acid
      phosphatase: GSP2

<400> SEQUENCE: 10

-continued

```
ctccatagca aaactcaaca agaacac                                    27

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 11
ggatccatct tcaagattag tttctct                                    27

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 12
tcataagtcg acactatagg gcacgcgtgg t                               31

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: primer
<223> OTHER INFORMATION: Primer 609BamL

<400> SEQUENCE: 13
ggatcctctg gtaaatcact tcctct                                     26
```

PHOSPHORUS-CONTROLLABLE RECOMBINANT EXPRESSION OF POLYPEPTIDES IN PLANTS

FIELD OF THE INVENTION

The present invention relates to materials and methods for the controlled expression of polynucleotides in plant cells.

BACKGROUND OF THE INVENTION

Biological methods for the production of economically valuable compositions of matter in the form of polypeptides have shown promise as alternatives to traditional chemical syntheses. Although several biological systems have been successfully explored as potential sources of polypeptides, including proteins, each system has been found to have its limitations.

The simplest and most thoroughly investigated biological methods for chemical production are microbiological systems. Primitive prokaryotic cells have been amenable to investigation and have been found to produce a variety of small organic and inorganic compounds, as well as a variety of complex biomolecules, such as homologous and heterologous polypeptides and proteins. The most extensively characterized prokaryote, *Escherichia coli*, synthesizes complex biomolecules using a relatively straightforward process of gene expression requiring minimal expression control elements and an uninterrupted coding region. Further, genetic elements encoding heterologous polypeptides can be introduced and expressed in *E. coli* without much difficulty. With these advantages, a wide variety of polypeptides have been expressed in a controlled manner in this organism. However, *E. coli* cultures do require the costly inputs of energy and nutrients. The organism also does not readily secrete the produced polypeptides, adding to the time and expense required to isolate the desired compound. Although other microbes, e.g., species of Bacillus, do secrete polypeptides into growth media, cultures of these organisms also require costly inputs of energy and nutrients. Moreover, all of these primitive prokaryotic systems exhibit additional shortcomings such as the expensive effort to avoid culture contamination and the inability of the microbes to properly process or derivatize many expressed polypeptides to fully biologically active forms.

Yeast and fungi are fairly primitive eukaryotic cells that have also been used to produce polypeptides, including heterologous polypeptides. Although these cells may do a better job of reproducing the natural derivatization of most commercially desirable (i.e., eukaryotic) polypeptides, the reproduction is imperfect. Additionally, cultures of yeast or fungal cells are susceptible to contamination and the cells themselves require valuable resources in the forms of energy and nutrients, Efforts to obtain the desired chemicals, such as heterologous polypeptides, are also burdened by the frequent need to extract the chemical from the cell and purify that compound from the chemically complex contents of the yeast cell released during extraction.

Animal cells, e.g. mammalian cells, although expected to closely approximate the native derivation of many important polypeptides (e.g., human polypeptides), are very costly to culture, due to their sensitivity to contaminants, their requirements for energy, gases, and nutrients, and their limited lifespans. Isolation of the produced chemicals also would be it relatively expensive in view of the typical inability of mammalian cells to secrete products and the relative chemical complexity of the intracellular environment of these cells.

Plants, as photoautotrophic organisms, provide an alternative to heterotrophic animals as life forms for the production of chemicals. Transgenic plants have been generated, albeit typically to improve the characteristics of the plants themselves (e.g., to confer resistance to disease, to improve the yield of edible foodstuffs). Nevertheless, some transgenic plants have been used to produce chemicals such as heterologous polypeptides. Some expression control sequences (e.g., regulatory elements, signal peptide sequences) have been found to function in plant cells, or to preferentially function in the cells of particular plant tissues and organs. For example, Sijmons et al. (U.S. Pat. No. 5,650,307) expressed Human Serum Albumin (HSA) by fusing the HSA coding region to the leader sequence from Alfalfa Mosaic Virus. This fused coding region was placed under the control of the Cauliflower Mosaic Virus 35S promoter and the Nopaline Synthase terminator. The HSA was expressed in transgenic potato plants and transgenic tobacco cells. Sijmons et al. further disclosed the secretion of HSA by potato plant cells and recovery of the heterologous HSA from the intercellular space of those plants. Of course, this recovery method involved the destruction of the potato plants.

U.S. Pat. No. 5,580,768 also discloses the production and secretion of heterologous protein by a plant. In particular, the '768 Patent discloses a transgenic rubber tree, with the expressed transgene protein being collected from wounds as a part of the latex. This system is highly specialized for use with Hevaea species (perennial tree species with slow growth), and the tree must be damaged by wounding to recover the heterologous polypeptide in the form of a latex mixture.

Transformed plant material has also been used to express heterologous polypeptides. Wongsamuth et al., Biotech. and Bioengineer. 54:401–415 (1997), report the use of hairy root cultures to express murine $IgG_1$ monoclonal antibody. Further, some antibody activity was found in the medium of the hairy root cultures maintained under axenic conditions as heterotrophic biomasses requiring costly energy and nutrient inputs.

In plant expression systems, as in other biological expression systems, maximal utility is realized by an expression system that is controllable. Control of the timing and extent of polypeptide expression reduces the costs involved in maintaining the typically transformed host cells because recovery can be initiated at times that are suitable for the polypeptide being expressed. For example, recovery can be coincident with the period during which expression is elevated when attempting to produce and purify a labile polypeptide. To maximize the yield of stable polypeptides required in quantity, the recovery period may lag the expression period. In still other cases, the production of toxic polypeptides is delayed until optimal numbers of producing cells are present, with little, if any, lag in the recovery period.

A variety of controllable expression systems have been identified in animal, bacterial, yeast, or fungal cells, and some of these systems are also found in plant cells. However, the majority of these systems suffer from disadvantages in terms of the simple, versatile and economic production and recovery of polypeptides from plant cells. Frequently, the small molecule effector responsible for controlling expression is difficult to make or costly to obtain and, for those effectors that are available, problems associated with toxicity are frequently encountered. These toxicity considerations include the toxic potential of the effector on the host cell, as well as the deleterious presence of the effector in the isolated polypeptide preparation.

Phosphorus is a nutrient that plays a central role in energy metabolism and, in the form of phosphate, is found in the nucleic acids of all living organisms. Much of the phosphorus available in the environment is not in a bioavailable form such as orthophosphate, however. Consequently, diverse organisms have developed capacities for transforming environmental phosphorus into bioavailable forms that are assimilated. These capacities are evident in the number and diversity of genes that respond to phosphorus levels. One class of genes encodes phosphatase enzymes, which can generally be divided into alkaline and acid phosphatases. Within a given organism, there is variation in the number and characteristics of acid phosphatases that are expressed.

Acid phosphatase expression has been studied most extensively in lower organisms such as yeast, fungi and bacteria. Phongdara et al., Appl. Microbiol. Biotechnol. 50:77–84 (1998), characterized a yeast acid phosphatase sequence and reported that expression of the gene could be repressed by phosphorus. However, the host cell was *H. polymorpha*, a methylotrophic yeast subject to the limitations of culturing identified above. Similarly, Ferminan et al., Microbiol. 143:2615–2625 (1997), characterized an acid phosphatase gene in another yeast species. The use of an acid phosphatase 5' control region to drive the expression of a heterologous gene has been reported for yeast (Kai et al., Seibutsu-Kogaku Kaishi 71:317–323 (1993), Ferminan et al., Appl. Environ. Microbiol. 64:2403–2408 (1998), Braspenning et al., BBRC 245:166–171 (1998), Shigematsu et al., J. Biol. Chem. 267:21329–21337 (1992)) and fungi (Macrae et al., Gene 132:193–198 (1993). The recombinant expression of bovine opsin, using an acid phosphatase signal sequence, has also been reported in yeast. Abdulaev et al., Protein Exp. Purif. 10:61–69 (1997). The expression of these acid phosphatase genes, and the use of acid phosphatase 5' control regions to express heterologous genes, has all been done in yeast and fungi, however. Thus, a need remains for a controllable expression system freed of the culture requirements and other problems attending use of these lower eukaryotic cells.

In vascular plants (i.e., multicellular plants including gymnosperms, angiosperms, ferns and liverworts, among others), acid phosphatases have received less attention. A review by Duff et al., Physiol. Plantarum 90:791–800 (1994), stated that some *Brassica nigra* acid phosphatases were induced by phosphate starvation in the context of noting that a wide variety of environmental and developmental factors (e.g., plant hormones, flowering, and senescence, among others) influenced APase activity, emphasized the heterogeneity of plant APases in terms of subunit structure, kinetic properties, and localization, and concluded that the available data demonstrated a lack of understanding of the molecular events underlying APase induction. Working with *Arabidopsis thaliana*, Patel et al., Plant Physiol. 111 (2 Supp.):81 (1996), reported the sequence of an acid phosphatase gene (Genbank Acc. No. U48448), while Williamson et al., Plant Physiol. 97: 139–146 (1991) disclosed a sequence of an APase gene from tomato. In addition to reporting an *A. thaliana* APase gene sequence, Patel et al. noted that steady-state levels of transcripts rose during phosphate starvation. Consistent with that observation, Trull et al. reported that acid phosphatase expression in *A. thaliana* could be de-repressed by lowering phosphorus levels. Trull et al., Plant Physiol. 105 (1 Supp.): 112 (1994); Trull et al., Plant, Cell and Environ. 20:85–92 (1997). This de-repression could be mitigated in the oilseed rape through the use of the fungicide phosphonate. Carswell et al., Planta 203:67–74 (1997). However, none of these reports disclose or suggest the use of the 5' control region of a vascular plant acid phosphatase to drive the expression of a heterologous gene in plant cells. Moreover, the *A. thaliana* acid phosphatase sequence (Genbank Acc. No. U48448) does not exhibit significant similarity to any lower eukaryotic acid phosphatase, confirming both the diversity of genes involved in phosphorus metabolism and the variation seen in the characteristics of acid phosphatase gene expression.

Thus, a need continues to exist in the art for a plant promoter capable of driving the expression of non-native coding regions in vascular plant cells, with that promoter being regulated by relatively simple, cost-effective techniques, such as controlling the bioavailability of phosphorus.

SUMMARY OF THE INVENTION

The present invention satisfies the aforementioned need in the art by providing a phosphorus-controllable plant promoter driving the expression of a non-native coding region (e.g., a transgene) in vascular plant cells. In the methods according to the invention, the non-native coding region is expressed in a plant cell, an intact plant portion, or a whole plant. Regulation of expression of the non-native coding region is achieved by controlling the level of at least one phosphorus compound delivered to a plant cell or by delivering a regulatory compound that affects a cell's level of bioavailable phosphorus. Suitable regulatory compounds include a phosphorus-depriving agent (i.e., an agent that deprives a plant cell of a physiologically significant amount of phosphorus), such as a phosphorus-sequestering agent, as well as a phosphorus-releasing agent, an agent that influences phosphorus transport into or out of a plant cell or an organelle thereof, or an agent that alters the distribution of phosphorus in bioavailable and non-bioavailable forms. Any type of phosphorus-depriving agent known in the art may be used in methods according to the invention. The simple and inexpensive expression methods of the invention may be used with any of a wide variety of vascular plant cells.

One aspect of the invention is directed to a method for expressing a non-native coding region in a vascular plant cell comprising the following steps: (a) transforming a vascular plant cell with a polynucleotide comprising a plant promoter controllable by a phosphorus compound operably linked to a non-native coding region, and (b) expressing the coding region. A coding region encodes an RNA or a polypeptide. A related aspect of the invention further comprises the step of controlling the level of the phosphorus compound by contacting the vascular plant cell with a regulatory compound. Thus, the methods extend to the use of all combinations of plant promoters controllable by phosphorus compounds and coding regions other than the operable linkage of a promoter controllable by a phosphorus compound to its natural or native coding region.

Another aspect of the invention is an isolated polynucleotide comprising a plant promoter controllable by a phosphorus compound operatively linked to a non-native coding region. A preferred plant promoter for use in the method is an acid phosphatase promoter. Also preferred is a plant promoter derived from a vascular plant source (e.g., members of the Brassicaceae family of plants, such as *Arabidopsis thaliana* and *Brassica juncea*). For example, a preferred plant promoter is selected from the group consisting of polynucleotides having sequences set forth in SEQ ID NO:1 (*A. thaliana* acid phosphatase promoter region; Genbank Acc. No. U48448), or fragments thereof having a minimum of 40 nucleotides, a recognizable −10 region having at least 90% similarity to the −10 consensus sequence(s) of eukaryotic promoters (e.g., TATRATG, where R is either A or G), and an element involved in expression control that is affected by phosphorus levels. In addition, the invention includes polynucleotides that hybridize to such polynucleotides under hybridization conditions of 3×SSC, 20 mM NaPO$_4$ (pH 6.8) at 65° C., and washing conditions of 0.2×SSC at 65° C.

Coding regions useful in the methods of the invention include polynucleotides from any source, natural or synthetic. The invention is not limited by the coding regions that may be operatively linked to promoters controllable by a phosphorus compound. Suitable coding regions encode animal RNAs or polypeptides, as well as variants, fragments and derivatives thereof The encoded products may be recovered for use outside the host plant cell (e.g., therapeutically active products) or they may alter the phenotype of the host plant cell (e.g., conferring disease resistance, the ability to survive or grow in the presence of particular substrates). Examples of such coding regions include polynucleotides derived from vertebrates, such as mammalian coding regions for RNAs (e.g., anti-sense RNAs, ribozymes, and chimeric RNAs having ribozyme structure and activity) or polypeptides (e.g., human polypeptide coding regions). Other coding regions useful in the inventive methods are derived from invertebrates (e.g., insects), plants (e.g., crop plants), and other life forms such as yeast, fungi and bacteria. The invention further contemplates any vector known in the art comprising a polynucleotide according to the invention.

Another aspect of the invention is a vascular plant host cell transformed with a polynucleotide according to the invention, regardless of whether such host cell is isolated or found in a plant material selected from the group consisting of an intact plant portion (e.g., a root, a shoot or a leaf) and a whole plant. Host cells according to the invention include the vascular plant host cells used in methods for producing coding region products according to the invention, as described below. A wide variety of floating, submerged, and soil-based plants are useful in the inventive methods, including monocots such as ryegrass, alfalfa, turfgrass, eelgrass, duckweed, and wilgeon grass as well as dicots such as tobacco, tomato, rapeseed, Azolla, floating rice, water hyacinth and any of the flowering plants. Additional plants capable of recombinant polypeptide expression also may be used in the methods of the invention. Presently preferred plant cells are derived from the Brassicaceae family of plants, including Brassica species, A. thaliana, and Nicotiana tabacum (i.e., tobacco).

As mentioned above, another aspect of the invention is a method for expressing a coding region product comprising the following steps: (a) transforming a vascular plant host cell with a polynucleotide selected from the group consisting of a plant promoter controllable by a phosphorus compound and a non-native coding region, and (b) maintaining the vascular plant cell under conditions that permit expression of a coding region operably linked to the promoter. Any of the sets of conditions known in the art, some of which are disclosed herein, is used. In one embodiment, a phosphorus-controllable plant promoter is transformed into a suitable plant host cell and the promoter becomes operably linked to a coding region in vivo. In another embodiment, a plant host cell is transformed with a non-native coding region that is operably linked in vivo to a promoter controllable by a phosphorus compound.

In some embodiments of the invention, recovery of the expressed product, such as an RNA or a polypeptide, is desired and is accomplished using any technique known in the art, including conventional invasive techniques that destroy plant tissue, such as vacuum infiltration and mechanical disruption. A preferred recovery technique avoids destruction of plant material by obtaining the expressed polypeptide from a plant exudate, in the case of whole plants or intact portions thereof, or secretions, in the case of isolated plant cells. In recovering polypeptides from plant exudates, the exudate is externally contacted with an aqueous medium to effect an admixture of the medium and the exudate in the process of recovery. The contacting step of the inventive processes may involve a culture system relying on soil-based cultivation or water-based cultivation such as hydroponics or aeroponics. The polypeptide is recovered from exudate, which may be root exudate, guttation fluid oozing from the plant as an exudate via leaf hydathodes, or other sources of exudate, regardless of xylem pressure. The contacting and recovering steps of the processes may be performed continuously or in a batch mode. In one embodiment, the polypeptide is expressed in, and recovered from, a plant portion. The plant portions for use in the processes of the invention are intact and living plant structures. These plant portions may be distinct plant structures, e.g., shoots, leaves, and roots. Alternatively, plant portions may be part or all of a plant organ or tissue, provided the material is intact and alive.

Figure 2:
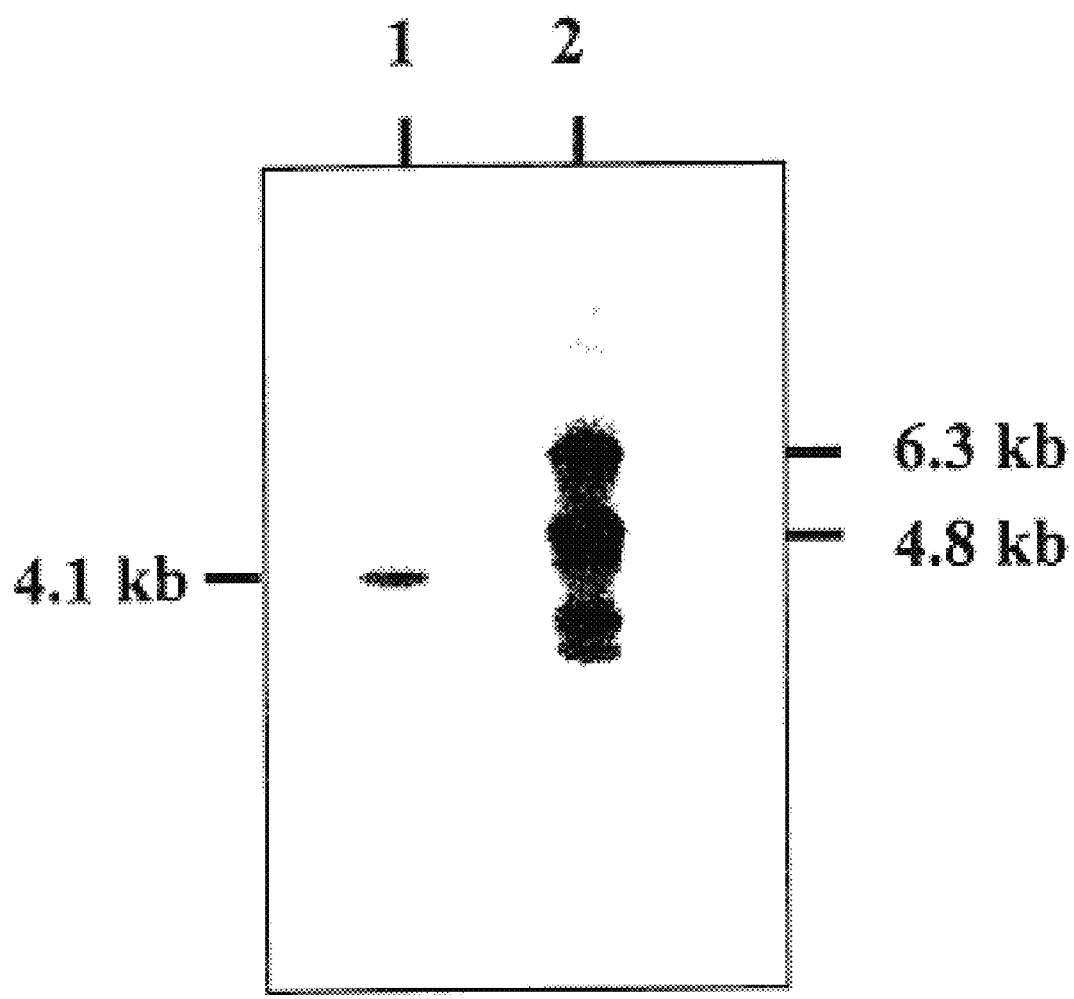
Figure 3:
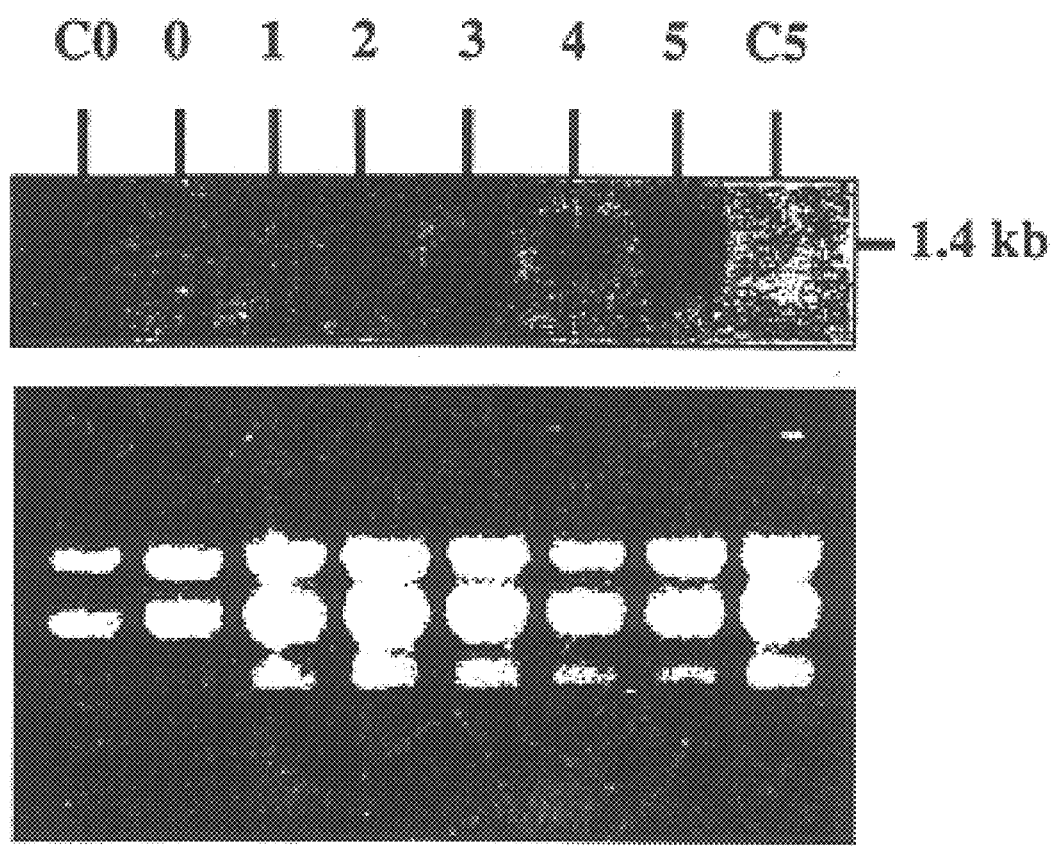

Numerous other aspects and advantages of the present invention will be apparent upon consideration of the following detailed description, reference being made to the drawing wherein:

FIG. 1 illustrates acid phosphatase expression by B. juncea roots;

FIG. 2 presents a Southern blot of plant genomic DNAS;

FIG. 3 shows a Northern blot of B. juncea MRNA and

FIGS. 4(A–H) and 5(A–F) illustrate non-native polypeptide expression in A. thaliana plants.

DETAILED DESCRIPTION OF THE INVENTION

The present invention provides versatile methods for the expression, and optional recovery, of a variety of coding region products using phosphorus-controllable plant promoters. RNAs and polypeptides are herein defined to include molecules of any length or sequence, and may be derivatized in any manner known in the art. Further, the definition of a polypeptide used herein extends to proteins and their fragments, whether single or multiple chain, and derivatized or not. These polypeptides are encoded by nucleic acids, which are operably linked to phosphorus-controllable plant promoters that facilitate the controlled expression of the desired polypeptides. "Controllable by a phosphorus compound" means "phosphorus-regulable" or "regulable by a phosphorus compound," insofar as the level of expression can be raised and/or lowered, or the timing of such expression can be manipulated, by intervention involving at least one phosphorus compound. A "plant promoter" is a promoter having a sequence derived from a vascular plant, rather than an animal or other form of life such as yeast, fungi, and bacteria. The plant promoter may be isolated from a natural source such as a plant cell or synthesized chemically. "Non-native" refers to unnatural operable linkages of plant promoters and polypeptide coding regions. Thus, a coding region operably linked to any phosphorus-controllable plant promoter other than the promoter to which it is linked in nature is referred to as a non-native coding region. Analogously, a "non-native" promoter controllable by a phosphorus compound is operably linked to any coding region other than the coding region to which it is linked in nature. A "heterologous" polynucleotide, by contrast, refers to the relative source of a polynucleotide. A coding region found in a particular vascular plant cell is a "heterologous" coding region if it is derived from any source other than the just-mentioned particular plant cell type. "Operably linked" in the context of plant promoters and coding regions, means an association of the two component structures such that the coding region is expressible from the plant promoter, regardless of the presence of additional expression control elements, and regardless of the extent of physical separation between the two components or the presence of intervening structures, such as other coding regions and/or expression signals. A "phosphorus compound" is any compound, organic or inorganic, containing a phosphorus atom. A preferred phosphorus compound is inorganic orthophosphate. A "bioavailable" phosphorus compound is a compound amenable to uptake by a biological cell, whether such cell is found in isolation or as part of an intact plant portion or whole plant. Any technique known in the art may be used to assess the bioavailability of a particular phosphorus compound. A "regulatory compound" is a compound that is capable of ultimately affecting the level of expression of a phosphorus-regulable promoter. Examples of regulatory compounds, as the term is used herein, include phosphorus compounds and phosphorus-depriving agents. A "phosphorus-depriving agent" is a compound that reduces the level of bioavailable phosphorus within a plant cell or an organelle of a plant cell. Examples of phosphorus-depriving agents are compounds that associate with phosphorus, such as any of the intercellular compounds involved in phosphorus metabolism (e.g., saccharides, including monosaccharides such as mannose and glucose, as well as polysaccharides), peptides capable of being phosphorylated, nucleosides and nucleotides, and other organic and inorganic compounds known in the art. Other types of regulatory compounds according to the invention are phosphorus-releasing compounds, compounds that affect phosphorus transport into or out of a plant cell or plant cell organelle, compounds capable of altering the distribution of phosphorus between bioavailable and non-bioavailable forms, and compounds that associate with phosphorus, such as phosphorus-sequestering agents.

In addition to the use of phosphorus-controllable plant promoters, the methods of the invention may include polynucleotides having a variety of other expression control elements, including enhancers, secretory signal sequences, tissue-specific expression elements, and terminators. These expression control sequences, in addition to being adaptable to the expression of a variety of gene products, afford a level of control over the timing and extent of expression. By concentrating this expression in plant materials, the invention eliminates costly requirements for energy, nutrients, and asepsis during expression.

The invention contemplates the recovery of some coding region products expressed in vascular plant host cells. When using whole plants or intact plant portions as hosts, the expressed coding region product is preferably recovered from a plant exudate. The term "exudate" is given its ordinary meaning of that which oozes out. In the context of plant biology, as applied herein, an "exudate" is a fluid that is or has, exited or oozed out of a plant or portion thereof, frequently as a result of xylem pressure, diffusion, or facilitated transport (i.e., secretion). Thus, the invention also minimizes costly post-expression manipulations to isolate the expressed coding region products. Further, the invention provides these benefits within the context of a system that is indefinitely sustainable.

The following examples illustrate presently preferred embodiments of the invention. Example 1 addresses the characterization of acid phosphatase activity in vascular plants. Example 2 describes the construction of recombinant plant polynucleotides for the controlled expression of polypeptides in vascular plants. Example 3 discloses the generation of transgenic plants by transformation with the recombinant polynucleotides. Example 4 addresses the expression of recombinant plant polynucleotides in vascular plants. Example 5 describes the construction of additional plant polynucleotides according to the invention. Examples 6–9 illustrate the expression, and optional recovery, of Xylanase (a prokaryotic enzyme), human placental Secreted Alkaline Phosphatase (SEAP), Green Fluorescent Protein (GFP, a eukaryotic protein), and Hepatitis B surface Antigen (HbsAg, a viral protein), respectively, using transgenic tobacco plants. Example 10 describes the expression and optional recovery of heterologous polypeptides using transgenic tomato plants (i.e., dicots). Example 11 provides a description of the expression (and possible recovery) of heterologous polypeptides using transgenic turfgrass (i.e., a monocot). Example 12 illustrates the recovery of a heterologous polypeptide from an exudate in the form of guttation fluid, using a soil-based cultivation system.

EXAMPLE 1

Characterization of Acid Phosphatase Activity in Vascular Plants

The expression and secretion of acid phosphatase (APase) was investigated in *Arabidopsis thaliana* and *Brassica juncea* plants using sensitive in vitro and activity gel assays. Phosphorus starvation induced two APases in *B. juncea* roots, only one of which was exuded. Northern blot analysis indicated transcriptional regulation of APase expression. PCR and Southern blot analyses revealed two APase homologs in *B. juncea*, whereas in *A. thaliana*, only one APase homolog was detected. The *A. thaliana* APase promoter region was cloned and fused to the GUS and GFP reporter genes, as described in the examples below.

Expression and secretion studies of *B. juncea* began with the germination of *B. juncea* seeds in Petri dishes on Gamborg's B-5 (Life Technologies, Gibco BRL, Grand Island, N.Y.) agar medium. Germinated seedlings were then transferred to 20 ml vials containing one-quarter-strength Hoagland's solution (Arnon et al., Soil Sci. 50:463–483 (1940)). Plants were grown in shaker-incubators (25 rpm), at 24° C. under a 16-hour photoperiod, with 150 mE/m$^2$/s illumination provided by a mixture of fluorescent and incandescent lamps. After 10 days, plants were transferred into 125 ml flasks with 120 ml of 0.25×Hoagland solution containing one of the following concentrations of phosphorus: 3 mM, 1 mM, 0.25 mM or 0.01 mM (i.e., phosphorus deficiency). In the low phosphorus medium, $(NH_4)_2SO_4$ was substituted for $NH_4H_2PO_4$. The volume of medium in each flask was adjusted daily to 120 ml and the exudate-containing media were sampled for APase activity.

Unconcentrated media samples were subjected to chromogenic determination at 410 nm. The activity of APase in the growth medium was determined using p-nitrophenyl-1-phosphate (p-NPP, Sigma Chemical Co., St. Louis, Mo.) as substrate and 50 mM Na-acetate buffer, pH 4.6, in a water bath at 37° C. (Ascencio, J., J. Plant Nutr. 20:9–26 (1997)). The reaction was stopped after 1 hour with a 1 M $Na_2CO_3$ solution and the yellow p-nitrophenol (PNP) was measured at 410 nm in a DU 640 Spectrophotometer (Beckman Instruments, Columbia, Md.). Results showed that after 6 days incubation in phosphorus-controlled media, samples from plants exposed to 3 mM, 1 mM, 0.25 mM, and 0.01 mM phosphorus had an $A_{410}$/(ml-hour) of approximately 0.04, 0.09, 0.21, and 0.33, respectively. Thus, expression of the exuded A. thaliana APase was de-repressed by phosphorus starvation.

For SDS-gel analysis, proteins in the medium were frozen, lyophilized, resuspended in $H_2O$ and dialyzed overnight against 50 mM Na-acetate buffer, pH 4.6. Proteins were stored at −20° C. until use. Extraction of intracellular root proteins was performed by homogenizing root tissue in liquid nitrogen using a pestle and mortar. Na-acetate buffer at 0.1 M, pH 5.4 (1 ml per 2 g of tissue) was added and the tissue was incubated on ice for 15 minutes. The mixture was centrifuged at 10,000×g for 30 minutes and the supernatant collected and stored at −20° C. until use. Protein concentration was determined as described by Bradford et al., Anal. Biochem. 7:248–254 (1976) using a commercial protein assay dye reagent (Bio-Rad Laboratories) and bovine serum albumin as a protein standard.

Concentrated protein samples were prepared in Laemmli buffer (Laemmli, U.K., Nature 227:680–685 (1970)) without 2-mercaptoethanol and were not boiled prior to gel loading. Proteins were separated by sodium dodecyl sulfate-polyacrylamide gel electrophoresis (SDS-PAGE) in 1.5 mm gels with 4% acrylamide (stacking gel) and 10% acrylamide (separating gel), in a Mighty Small II protein electrophoresis cell (Hoefer Scientific Instruments, San Francisco, Calif.).

For activity determinations, enzymes were reactivated in situ by removing the SDS, following the casein/EDTA procedure described by McGrew et al., Anal. Biochem. 189:68–74 (1990). After SDS removal, gels were washed four times using a 0.1 M Na-acetate buffer at pH 4.6. The substrate used for the activity assay was 4-methylumbelliferyl-phosphate (4-MUP) (cat. no. M-8168, Sigma Chemical Co.), which, upon hydrolytic removal of the phosphate group, produced fluorescent 4-methylumbelliferone. Enzyme activity was detected by overlaying the gel with the 4-MUP substrate at 300 µg/ml in 100 mM Na-acetate, pH 4.6, mixed with 1% low-melting-point agarose. The gels were viewed under UV light. FIG. 1 shows the results of such an experiment, where lanes 1 and 3 each contained 50 µg of root protein extract and lanes 2–4 each contained 5 µg of exuded root protein. Further, the samples loaded in lanes 1 and 2 came from B. juncea roots incubated for 9 days in medium containing 1 mM phosphorus, lanes 2 and 4 contained samples of B. juncea root cultures incubated in medium containing 0.01 mM phosphorus, a phosphorus-starvation condition. Significantly more fluorescent product indicative of APase activity is seen under phosphorus starvation conditions compared to adequate phosphorus conditions.

EXAMPLE 2

Plant APase Polynucleotides

DNA was isolated from B. juncea and A. thaliana plants using the Phytopure plant DNA extraction kit (Nucleon Biosciences, Lanarkshire, UK). For Southern blot analysis, genomic DNAs were digested with EcoRI, electrophoresed through a 1% agarose gel, and transferred to Hybond-N$^+$ nucleic acid transfer membrane (Amersham, Piscataway, N.J.). The 1,100 bp A. thaliana APase probe was gel purified and radiolabeled with $^{32}$P by random priming according to standard procedures (Sambrook et al., 1989). The results are shown in FIG. 2, where 5 µg of A. thaliana DNA was loaded in lane 1 and 10 µg of B. juncea DNA was loaded in lane 2. As shown in the Figure, a 4.1 kb EcoRI fragment of genomic DNA was identified using A. thaliana DNA; 4.8 kb and 6.3 kb EcoRI fragments of B. juncea DNA were identified.

For Northern blot analysis, RNA was isolated from B. juncea roots using the RNeasy plant mini kit (Qiagene, Valencia, Calif.), electrophoresed, and blotted according to the manufacturer's instructions. The 900 bp B. juncea APase probe was gel purified and radiolabeled with $^{32}$P by random priming as described above. The results, shown in FIG. 3, identify a 1.4 kb message expressed in phosphorus-starved B. juncea roots (upper panel). The lower panel of FIG. 3 shows amounts of total RNA loaded in each lane (lane $C_o$-control plant at day 0 grown in 1 mM (i.e., standard) phosphorus medium; lanes 0–5- plants grown in 0.01 mM phosphorus for 0–5 days, respectively; lane $C_5$- control plant at day 5 grown in standard phosphorus medium). Thus, the expression of the 1.4 kb message is specific to the phosphorus-starvation condition and is not a quantitative artifact.

To amplify APase gene fragments, four 21-bp-long oligomers from the A. thaliana APase coding region were designed to be used as PCR primers. Two upper primers were synthesized: 568U (5'-TTGTTGAGTTTTGCTATGGAG-3'; SEQ ID NO:5) starting at position 568 and 608U (5'-CAGAGGAAGTGATTTACCAGA-3'; SEQ ID NO:6) starting at position 608, and two lower primers: 1383L (5'-TATCCCATCTATTGTTGTCGT-3'; SEQ ID NO:7) starting at position 1,383 and 1561L (5'-ACGCCCTTTTGATGGAATACC-3'; SEQ ID NO:8) starting at position 1,561. (All positional references are to SEQ ID NO:1.) PCR reactions were performed using the Gene-Amp PCR System 9700 (PE Applied Biosystems, Foster City, Calif.). DNA sequencing was performed using ABI 377 Dye-Terminator Cycle Sequencing.

GenomeWalker libraries were prepared from A. thaliana using the Universal Genome Walker Kit (Clontech, Palo Alto, Calif.), by digesting the DNA with five enzymes generating blunt ends. The genomic fragments were then ligated to specific adapters provided in the kit, resulting in five "Genome Walker libraries."

Two gene-specific primers (GSP1 and GSP2) were designed using the A. thaliana APase gene sequence: The sequence of GSP1 is 5'-TGTCATCTGGTAAATCACTTCCTCT-3' (SEQ ID NO:9); the sequence of GSP2 is 5'-CTCCATAGCAAAACTCAACAAGAACAC-3' (SEQ ID NO:10).

Cloning the APase promoter region was facilitated by using these primers for amplification of the APase 5' regions as detailed in the Universal Genome Walker Kit user manual (Clontech). The fragments resulting from the PCR reactions performed on the GenomeWalker libraries were sequenced. Sequences upstream (i.e., 5') of the APase gene were analyzed for regulatory sequences and promoter-like elements, and signal peptide sequences were identified.

To clone the DNA fragment containing the APase promoter region into the binary plant transformation vector PB 101.1, which contains a promoterless GUS cassette (Clontech), a new primer, 504BamL, was synthesized. This primer was designed to amplify the promoter region and to create a BamHI restriction site in the 3' end of the amplified fragment (the BamHI site is indicated by the underlined bases): 5'-GGATCCATCTTCAAGATTAGT-TTCTCT-3'; SEQ ID NO:11. Another primer, AP2-SalI, was designed to create a SalI site at the 5' end of the amplified fragment: 5'-TCATAAGTCGACACTATAGGGCACGCGT-GGT-3'; SEQ ID NO:12. These primers were used to amplify the promoter region. The resulting fragment was digested with BamHI and SalI, gel purified, and cloned into corresponding sites in PB101.1, a plant transformation vector. The resulting plasmid, Pr-GUS, was used to transform A. thaliana plants.

In order to fuse the APase promoter and its signal peptide in-frame with the GFP (i.e., enhanced GFP) sequence, a primer corresponding to 10 amino acids downstream of the cleavage site of the mature secreted APase was synthesized. This primer, 609BamL (5'-GGATCCTCTGGTAAATCACTTCCTCT-3'; SEQ ID NO:13), was designed to create a BamHI restriction site in the 3' end of the amplified fragment. This primer and the AP2SalI primer were used to amplify the promoter region and the signal peptide coding region. The resulting fragment was digested with BamHI and SalI, gel purified, and cloned into the pEGFP vector (Clontech Laboratories), which encodes an enhanced GFP having an amino acid substitution (S65C). The plasmid containing the BamHI-SalI fragment was digested with SalI and StuI (produces blunt ends) and the fragment containing the promoter, signal peptide, and the EGFP gene was gel purified. The PB101.1 plasmid was digested using SalI and EcoICRI (produces blunt ends) and the fragment containing the GUS gene was separated from the vector by electrophoresis. The PB101.1 vector fragment was gel purified and ligated to the fragment containing the APase promoter, the signal peptide coding region, and the EGFP gene. The resulting plant transformation vector, designated PS-GFP, was used to transform A. thaliana plants.

EXAMPLE 3

Plant Cell Transformation

Recombinant polynucleotides were separately introduced into plants using *Agrobacterium tumefaciens*. The streptomycin-resistant *Agrobacterium tumefaciens* strain LBA4404 was transformed with recombinant polynucleotides using the freeze-thaw procedure described by Hood et al., J. Bacteriol. 168: 1291–1301 (1986). Transformation of *Agrobacterium tumefaciens* LBA4404 was optionally confirmed by Southern DNA hybridization. Any of the conventionally known and available plant transformation vectors and *A. tumefaciens* strains may be used.

*A. thaliana* (Columbia ecotype) plants were then transformed with Agrobacterium harboring the polynucleotides described herein using the Agrobacterium vacuum infiltration method (Bent et al., Science 265:1856–1860 (1994); Bechtold et al., Life Sciences 316:1194–1199 (C. R. Acad. Sci., Paris, 1993)) and were grown in pots containing Premier Promix (Riviere-du-Loup, Quebec, Canada) for seed production. The seeds were plated on agar-Murashige and Skoog (MS) medium (Sigma Chemical Co.) containing 10 g/L sucrose, supplemented with 500 mg/L cefotaxime and 100 mg/L kanamycin. Transformed T1 seedlings were selected and grown in pots for seed production. T2 seeds were germinated on phytagel (Sigma) plates containing MS medium with 10 glL sucrose, and transferred after 5–7 days into LifeRaft membrane rafts in culture boxes (107×107×96 mm high) (Gibco BRL) containing 150 ml liquid MS medium with 10 g/L sucrose. The plants were grown in shaker-incubators under the conditions described above. Seedlings were tested for neomycin phosphotransferase II expression (NPTII) using the PathoScreen kit (Agdia, Elkhart, Ind.) after incubation for 7 days. T2 plants showing expression of the NPTII protein were transferred into a hydroponic system consisting of a glass vial containing sterile, liquid 0.25×Hoagland medium with or without phosphorus (0.25 mM).

Beyond the traditional use of Agrobacterium-based transformation protocols to transform dicots, continued efforts have shown that Agrobacterium-based methods may also be employed to transfer non-native nucleic acids to monocot species in the generation of transgenic plants for use in methods according to the invention. Smith et al, Crop Science 2:301–309 (1995), incorporated herein by reference.

Other transformation methodologies may also be employed to generate transgenic plants, as would be understood in the art. For example, direct DNA transfer into plant cell protoplasts may be effected by the conventional techniques of calcium phosphate co-precipitation, the use of poly-L-ornithine, liposome-mediated transformation, electroporation, microinjection or fusagen-mediated (e.g., polyethylene glycol) transformation, and plants regenerated from the transformed protoplasts. PCT/US84/00050 and Christou, Euphytica 85:13–27 (1995), each incorporated herein by reference. Other transfer methodologies such as biolistic transformation (i.e., microprojectile or particle bombardment) do not require plant cell protoplasts, thereby simplifying the process of regenerating transgenic plants. Consequently, biolistic transformation may be employed to introduce the coding region for a heterologous polypeptide into a wide variety of plants, including both monocots and dicots. Christou (1995); Jahne et al., Euphytica 85:35–44 (1995), incorporated herein by reference.

Regeneration of transgenic plants from transformed cells, including transformed protoplasts, may be accomplished using any one of several techniques known in the art. Several approaches to the regeneration of transgenic plants are disclosed in EP-A-0 243 553, incorporated herein by reference. These approaches include regeneration via embryogenic or organogenic routes. Alternatively, plants may be regenerated following transformation by a method that incorporates a step for inducing meristem reorganization to improve the chances of transgenic cells contributing to the germline, followed by a step providing conditions promoting differentiation of meristem. PCT/US95/08977, incorporated herein by reference. In general, any of the transformation and regeneration methodologies known in the art may be used to generate transgenic plants for use in methods according to the invention.

One of ordinary skill in the art will appreciate that polynucleotides of the invention comprising either a promoter controllable by a phosphorus compound or a non-native coding region become operatively linked within the vascular plant host cells. To facilitate that operative linkage, e.g., by homologous recombination, such polynucleotides may also contain sequences that promote targeted integration by site-directed recombination of the polynucleotide into a polynucleotide found in the plant cell (e.g., a plant chromosome or episome).

EXAMPLE 4

Recombinant Coding Region Expression

Figure 4A:
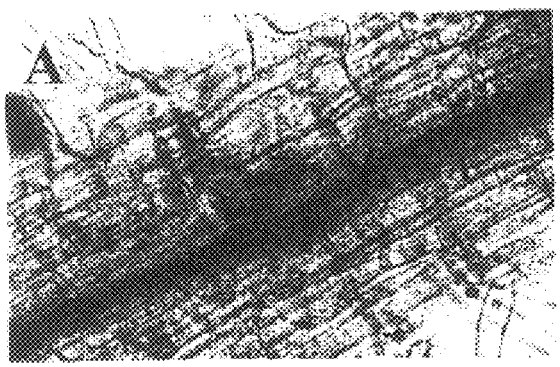
Figure 4B:
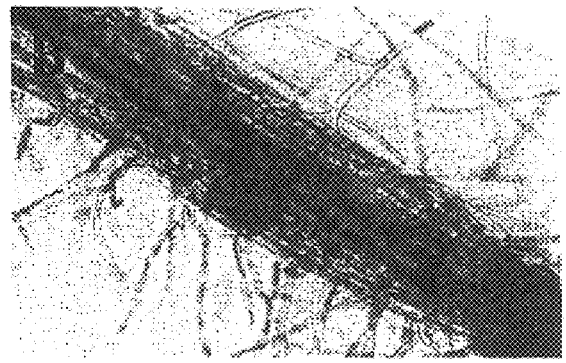
Figure 4C:
Figure 4D:
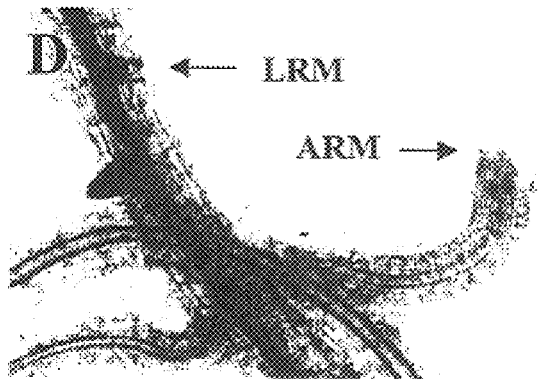
Figure 4E:
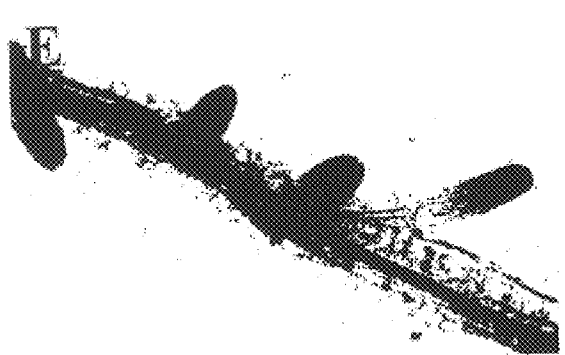
Figure 4F:
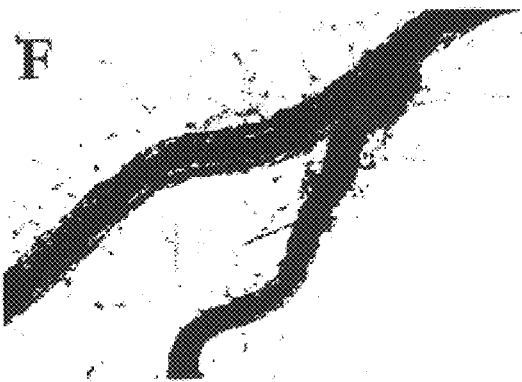
Figure 4G:
Figure 4H:
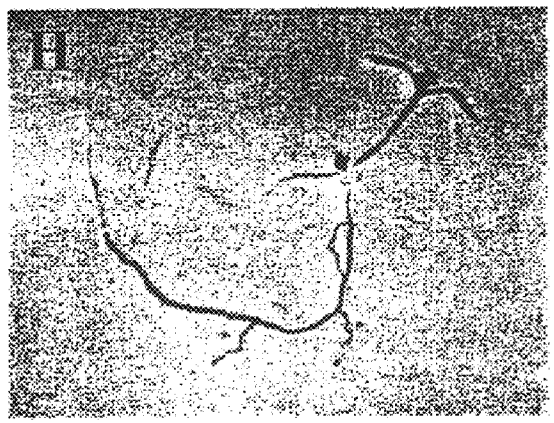

A screening method was developed to evaluate GUS expression levels in the various transformed lines: T2 seedlings were germinated in pots containing fine granules of washed sand (40–100 mesh Fisher Scientific, Pittsburgh, Pa.). To remove trace amounts of contaminating elements, the sand was previously washed by soaking it in 0.1 M HCl for 45 minutes and then washing it extensively with ddH$_2$O until the sand mixture reached pH 6.5. Seedlings were grown in standard phosphorus medium for 14 days before transfer to phosphorus-deficient medium. GUS expression in plants subjected to phosphorus-deficient conditions for 14 days is shown in FIGS. 4A–4D (FIG. 4A—lateral root primordium with localized GUS expression, FIG. 4B—GUS expression in several cell layers of lateral root primordium; FIG. 4C—emerging lateral root meristem; FIG. 4D—lateral root meristems (LRM) and an apical root meristem (ARM)). GUS expression in plants starved for phosphorus for 17 days is shown in FIG. 4E. Seedlings were also germinated in pots containing washed sand, and then fertilized using 0.25× Hoagland's medium with or without phosphorus (0.25 mM), and examined after 10 days. GUS expression in the roots of these seedlings (FIG. 4F) or in the whole seedlings (FIG. 4G—not starved; FIG. 4H—starved) is shown. Phosphorus starvation symptoms were evident 8 days after sowing. Plant expression was examined by staining with x-gluc (i.e., 5-bromo-4-chloro-3-indolyl β-D-glucuronide), as described below, to evaluate GUS expression.

GUS activity was determined according to the method of Jefferson et al., EMBO J. 6:3901–3907 (1987). After staining, tissue was fixed in 1.5% formaldehyde-4% acetic acid-30% ethanol for 30 minutes, dehydrated through a graded ethanol series (50, 95, 100% for 20 minutes at each step), incubated 2 hours at 100% ethanol, and rehydrated through a graded ethanol series (95 and 50%, for 20 minutes each step). Rehydrated tissues were stored in H$_2$O.

Similar methods were used to evaluate the recombinant expression of EGFP. Recombinant expression of GFP under the control of the APase promoter was performed using *A. thaliana* plants. As when expressing GUS in transformed *A. thaliana*, plants were grown for 14 days in standard 1 mM phosphorus medium and transferred to phosphorus starvation (0.01 mM phosphorus) conditions. Wild-type plants subjected to the same growth regimen were used as controls. The results are presented in FIGS. 5A–5F (FIG. 5A—photomicrograph of transformed roots showing the root tip and branching root meristem; FIG. 5B—fluorescence photomicrograph of the roots shown in FIG. 5A; FIG. 5C—photomicrograph of wild-type root meristem; FIG. 5D—fluorescence photomicrograph of the roots shown in FIG. 5C; FIG. 5E—Wild-type (left) and transformed *A. thaliana* grown in hydroponic media; FIG. 5F—ultraviolet photomicrograph of GFP exudation from wild-type (left) and transgenic (right) *A. thaiana* plants). Thus, the transformed *A. thaliana* plants recombinantly expressed and exuded GFP.

EGFP and GUS visualization and documentation were performed using an Eclipse TE200 Inverted microscope (Nikon, Tokyo Japan). The images were captured with a 3-CCD camera (24 bit) using Optronics DEI-750CE hardware. EGFP detection was performed using a single band filter set 31039 JP1 with D470/20 nm exciter, D510/20 nm emitter and 490 dc/p beamsplitter (Chroma Technology Corp., Brattleboro, Vt.). GUS detection was performed using a halogen lamp. Nikon objective lens specifications were: magnification ×10 with Numerical Aperture (NA) 0.25 and a phase contrast Ph1; magnification ×20 with NA 0.45, and a phase contrast Ph1; magnification ×40 with NA 0.6 and a phase contrast Ph 2. Photomicrographs of the *A. thaliana* seedlings were taken with a 35 mm Nikon 4–401S camera.

Results showed that the expression of GUS in phosphorus-starved roots was first evident in lateral root meristems followed by generalized expression throughout the root. GUS expression was also detected in the leaves of phosphorus-starved plants. The expression of GUS diminished with the addition of phosphorus to the medium. Expression of GFP was also first evident in the lateral root meristems and recombinant GFP was secreted by the phosphorus-starved roots into the medium.

Pr-GUS transformants, germinated and grown in sand culture, were used to test the specificity of APase promoter induction by either inducing nutritional deficiencies other than P-limitation or by using such known chemical inducers of gene expression as salicylic acid (Ward et al., Plant Cell 3:1085–1094 (1991)) and jasmonic acids (Staswick, et al., Plant Physiol 96:130–136 (1991), Creelman et al., New Phytol. 75:479–490 (1992)) (Tables 1 and 2). Seedlings were germinated in pots containing washed sand and fertilized with modified 0.25×Hoagland's medium optionally lacking nitrogen (N), potassium (K), or iron (Fe). Nitrogen-free Hoagland's medium was prepared by substituting K$_2$HPO$_4$ for (NH$_4$)$_2$SO$_4$, CaSO$_4$ for Ca(NO$_3$)$_2$ and K$_2$SO$_4$ for KNO$_3$. Potassium-free Hoagland's medium was prepared by substituting NaNO$_3$ for KNO$_3$. Iron deficient medium was prepared by removing Fe-EDTA from the medium composition. Aqueous solutions of salicylic acid (SA), jasmonic acid (JA), and mannose were supplied to 14-day-old seedlings by spraying until solutions ran off the seedlings; approximately 20 ml of 2.5-fold concentrated solution was added to the sand at the same time.

Both chemical inducers were applied at concentrations capable of strongly inducing a variety of plant genes. These treatments were compared to the effects of P removal (Table 1, where "P" is phosphorus, N is nitrogen, K is potassium, and Fe is iron, "+" indicates presence and "−" indicates absence, and relative expression is indicated on a scale of "−" (lowest), "+/−," "+," "++," to "+++" (highest)) or the addition of mannose (Table 2, where is indicated on a scale of "−" (lowest), "+/−," "+," "++," to "+++" (highest)). Mannose is known to induce P deficiency in plant cells by virtue of its ability to bind cellular phosphates as mannose 6-phosphate (Watkins, et al., Plant Physiol. 97:139–146 (1987)), thereby acting as an agent that associates with a phosphorus compound. Therefore, mannose-induced P-starvation is used as a tool to study P metabolism and utilization in plant tissues (Herold, et al., New Phytol. 791–40 (1977). Gus activity was strongly and consistently induced only in P-starved seedlings regardless of whether starvation was induced by withholding P or by supplying mannose (to effectively lower the concentration of available phosphorus). Mannose had toxic effects at high concentrations (at least 50 mM). Monitoring of spatial and temporal patterns of GUS expression in sand-grown Arabidopsis seedlings deprived of P revealed an initial strong induction in the apical meristem approximately 5 days after sowing, followed by expression in the shoots, leaves, and roots, with the whole seedling expressing GUS by approximately day 6–7. Seventeen days after sowing, the experiment was terminated.

TABLE 1

| Days after seeding | +P | -P | -N | -K | -Fe |
|---|---|---|---|---|---|
| 7 | - | + | - | - | - |
| 9 | - | +++ | - | - | - |
| 11 | - | +++ | - | - | - |
| 13 | - | +++ | - | - | - |
| 15 | - | +++ | - | - | - |
| 17 | - | +++ | - | +/- | + |

TABLE 2

| Days after Treatment | 100 μM salicylic acid | 100 μM jasmonic acid | 5 mM mannose | 20 mM mannose | 50 mM Mannose |
|---|---|---|---|---|---|
| 1 | - | - | - | + | ++ |
| 3 | + | - | - | + | +++ |
| 5 | - | - | + | + | ND |
| 7 | +/- | - | - | ++ | ND |

The data indicate that the APase promoter can be used to simply and effectively regulate the expression of transgenes in *A. thaliana*. More generally, the inducible APase promoter is expected to be useful in expressing a wide variety of prokaryotic, eukaryotic, viral, and synthetic coding region products (e.g., polypeptides) in a wide variety of vascular plant cells because the promoter exhibits the following characteristics: (i) it is responsive to a simple and environmentally benign chemical; (ii) it can be up-regulated by lowering P levels and down-regulated by restoring P supply; (iii) the basal level of expression is relatively low (iv) the induction occurs throughout the plant; and (v) the induction is relatively strong and P-specific.

The preceding description of the recombinant expression of GUS and EGFP illustrate the advantages of using a polynucleotide comprising the sequence set forth in SEQ ID NO: 1 to provide control over that expression using, e.g., simple and inexpensive forms of bioavailable phosphorus. Other polynucleotides providing a phosphorus-controllable plant promoter region are also embraced by the invention. Fragments of the above-described plant promoter polynucleotide may also be used, provided that such fragments retain at least the capacity to drive the expression of an operably linked non-native coding region in a manner that permits expression regulation by altering the bioavailability of a phosphorus compound. For example, a preferred plant promoter polynucleotide fragment of the invention comprises nucleotides 1–1189 of SEQ ID NO:1. Other fragments according to the invention have at least 40 nucleotides and exhibit at least 90% similarity to the consensus "TATA" box ("TATRATG"), as determined by the BLASTN program available from the U.S. National Center for Biotechnology Information. Polynucleotide derivatives contemplated by the invention include polynucleotides having sequences showing the substitution of modified nucleotides, e.g. inosine-based nucleotides, for conventional nucleotides such as GMP. Variant polynucleotides of the invention include polynucleotides that hybridize to a polynucleotide comprising the sequence set forth in SEQ ID NO:1 under hybridization conditions of 3×SSC, 20 mM NaPO$_4$ (pH 6.8) at 65° C., and washing conditions of 0.2×SSC at 65° C. Preferred polynucleotides have sequences of at least 40 nucleotides that exhibit 95%, 98%, 99%, or 99.9% similarity to a sequence set forth in SEQ ID NO:1, as determined using the algorithm implemented in the BLASTN program.

Beyond the controllable promoters per se, the invention comprehends the operable linkage of a signal peptide coding region to facilitate secretion of polypeptides from plant cells. Any of the signal peptide coding regions known to be operative in plant cells may be used. An example is the signal peptide coding region of *A. thaliana* acid phosphatase (nucleotides 504–596 of Genbank Acc. No. U48448). As noted above, additional regulatory elements known in the art (e.g., enhancers, gene-specific control elements, terminators) may also be found in polynucleotides according to the invention. Exemplary polynucleotides are described in greater detail below.

EXAMPLE 5

Polynucleotides

The plasmid pNBAP-CAR-GFP is used to recombinantly express the green fluorescent protein (GFP) under the control of the *A. thaliana* APase promoter (SEQ ID NO:1) and the Calreticulin signal peptide coding region. Construction of pNBAP-CAR-GFP proceeds in several steps. The GFP coding region is obtained from, e.g., the pUC-based plasmid pCK GFP S65C, which contains the S65C-modified GFP (i.e., EGFP) coding sequence, as described in Heim et al., Nature 373:663–664 (1995). The modification, a change in codon 65 resulting in a substitution of Cysteine for Serine (S65C), resulted in a six-fold increase in the intensity of green fluorescence, as reported by Reichel et al. Proc. Natl. Acad. Sci. (USA) 93:5888–5893 (1996).

To direct GFP into the secretory pathway, the GFP coding region is fused to the coding region for a tobacco signal peptide, to wit, the endoplasmic reticulum resident protein Calreticulin (CAR). A cDNA fragment coding for the Calreticulin N-terminal signal peptide of 27 amino acids, along with the upstream 21 bp 5'-untranslated sequence, is amplified by PCR using forward Clamp 1b: 5'-GGTTCGAATTCGATCTCACAACAGTGGGCATGG-3' (SEQ ID NO:2) and reverse Clamprev: -5CTCTTTAAACCATGGAGACCTCAGCGGAGAC GAC-3' (SEQ ID NO:3) primers and the plasmid Cal1-Np1 containing the full-length Calreticulin cDNA (Genbank Accession No. Z71395) as an amplification template. The amplified fragment contains the Calreticulin signal peptide coding region flanked by restriction sites SfuI and EcoRI at the 5' terminus, and NcoI and DraI sites at the 3' terminus. The forward primer Clamp 1b was designed such that the NcoI site (5'-CCATGG-3') located in the 5'-untranslated region of Cal1-Np1 was destroyed by replacing the 5' "C" with a "G." The reverse primer was designed to place an NcoI site in the Calreticulin signal peptide coding sequence at a position two codons downstream from the encoded signal peptide (SP) cleavage site, thereby creating an NcoI site useful in fusing the Calreticulin signal peptide coding region to a heterologous polypeptide coding region, such as the GFP coding region. At positions -9 to -12 of the 5' untranslated region of Calreticulin mRNA is an AACA sequence for efficient translation initiation in plants.

A PCR-amplified DNA fragment encoding the Calreticulin signal peptide is cloned into dephosphorylated pUC18 at the SmaI site using the SureClone Ligation kit (Pharmacia, Inc.) to generate the plasmid pNBCAR. The Calreticulin signal peptide-GFP fusion is carried out by cloning the NcoI-XbaI fragment of plasmid pCK GFP S65C into the NcoI and XbaI sites of pNBCAR to generate pNBCAR-GFP. The fusion point is confirmed by sequence analysis of pNBCAR-GFP. To place the CAR-GFP fused coding region under the control of the APase promoter, pNBCAR-GFP was digested with EcoRI and SalI and the fragment containing the fused coding region was isolated following agarose gel electrophoresis. This fragment was then rendered blunt-ended by a standard fill-in reaction with deoxynucleoside triphosphates and the Klenow fragment of DNA polymerase I. Plasmid Pr-GUS is used as a source for the APase promoter. This plasmid was digested with SalI and EcoICRI to release the GUS coding region. Following Mung Bean nuclease digestion to blunt the ends of the vector fragment of Pr-GUS, the DNA fragment containing CAR-GFP is inserted to generate pNBAP-CAR-GFP. Proceeding in the 5'-3' direction, pNBAP-CAR-GFP contains the selectable marker, the APase promoter, the CAR signal peptide coding region, the GFP coding region, and a terminator for the GFP expression unit.

Recombinant expression of SEAP is also directed by the APase promoter. The plasmid used for this expression, pNBAP-CAR-SEAP, is constructed by inserting the SEAP coding region into the plasmid pNBCAR. The SEAP coding region is excised from the pSEAP2-Enhancer plasmid using XhoI and XbaI. Again, the overhanging ends are filled using Klenow and the standard deoxynucleoside triphosphates. The plasmid pNBCAR is prepared by restriction with XbaI, Mung Bean exonucleolytic digestion, and dephosphorylation. Insertion of the fragment containing the SEAP coding region into the blunted XbaI site of pNBCAR generated pNBCAR-SEAP. The fused CAR-SEAP coding region is then excised from pNBCAR-SEAP and used to replace the GUS coding region in Pr-GUS, as described above. The resulting plasmid, PNBAP-CAR-SEAP, is used in practicing the methods of the invention.

Recombinant expression of Xylanase using a phosphorus-controllable plant APase promoter is also contemplated by the invention. An approach similar to the construction of pNBAP-CAR-SEAP is chosen, with the Xylanase coding region prepared either as a blunt-ended fragment using PCR and the published Xylanase sequence, or by excising the Xylanase coding region from pBinAR-XynZ (Herbers et al., Bio/Technology 13:63–66 (1995)). In using pBinAR-XynZ as a source for the Xylanase coding region, the plasmid is digested with suitable restriction endonucleases, e.g. KpnI and XbaI, followed by blunt ending of the fragment using any conventional technique such as Klenow-mediated fill-in reactions or mung bean exonuclease digestion. Ligation of a fragment containing the Xylanase coding region into suitable blunt-ended site(s) of pNBCAR is accomplished using well-known techniques. The resulting plasmid, pNBCAR-Xyn, is then restricted and the fused CAR-Xyn coding region is substituted for the GUS coding region in Pr-GUS, as described above. The resulting plasmid, pNBAP-CAR-Xyn, is used in practicing methods according to the invention. One of ordinary skill in the art is aware that these approaches to the construction of recombinant molecules according to the invention can be applied to a wide variety of coding regions, rendering the expression of such coding regions in plants controllable by manipulating phosphorus bioavailability.

The invention contemplates methods involving plasmids, including the plasmids described above. Additionally, other means for introducing the phosphorus-controllable plant promoters, optionally in operative linkage to a non-native coding region, into plants are contemplated by the invention. Viruses, bacterial genomes, plasmids, phagemids, cosmids, and other vectors may be employed as long as they are functional in delivering the polynucleotides of interest to the desired cells. Preferred vectors encode alectable marker to facilitate identification of recombinant plant cells. The invention also embraces non-vector-Qbased methods for introducing the polynucleotides of the invention, e.g., ballistic methods for polynucleotide introduction; the invention also contemplates transformation of plant cell protoplasts with polynucleotides that may be either transiently expressed or integrated into a resident polynucleotide and expressed.

EXAMPLE 6

Expression of Xylanase using Transgenic Tobacco Plants

Transgenic tobacco plants containing a Xylanase coding region under the control of a plant APase promoter are generated as described above using, e.g., pNBAP-CAR-Xyn. Following root formation, hydroponic cultivation is initiated by placing the transgenic plants into sterile liquid MS medium containing 15 g/L of sucrose, 500 mg/L cefotaxime and 100 mg/L of kanamycin. Wild-type control plants (i.e., untransformed plants in this Example) are cultivated in a similar medium without antibiotics. Plants are positioned in a synthetic stopper to permit the roots to contact the medium under sterile conditions while the remainder of the plants (i.e., plant regions above the hypocotyl under normal gravimetric culture conditions) are in an open and non-sterile environment.

Beginning approximately 2–3 weeks after rooting, exudates are periodically sampled by aspiration of medium with sterile syringes. The protein content of intercellular fluids is also examined. Intercellular fluids are isolated as described by Parent et al., Can. J. Bot. 62:564 (1984), with some modifications. After washing with water, freshly harvested roots or leaves are infiltrated with an appropriate ice-cold buffer (50 mM Na-acetate buffer, pH 5.9) under vacuum. Infiltrated tissues are centrifuged at 350×g for 15 minutes to isolate the intercellular fluid. Intercellular proteins are concentrated by ultrafiltration (Microcon 10 membranes having a 10 kD cut-off, Amicon, Inc.) Samples are incubated at 65° C. for 30 minutes to denature thermolabile proteins (GFP, SEAP and Xylanase are heat stable), rapidly cooled on ice, and stored at −20° C.

Xylanase assays are performed essentially as described by Biely et al., Methods Enzymol. 160:536–542 (1988). In brief, RBB-xylan (11.5 mg/ml; Sigma Chemical Co.) is incubated at 60° C. for 20 minutes with protein extract in a final volume of 240 $\mu$l 150 mM sodium acetate (NaOAc), pH 5.4. The reaction is stopped by adding 480 $\mu$l of 96% ethanol. After standing at room temperature for 30 minutes, the precipitate is removed by centrifugation for 3 minutes at 15,000×g. The smaller blue-stained fragments found in the supernatant indicate Xylanase activity.

Detection of Xylanase by native polyacrylamide gel electrophoresis (PAGE) is also carried out according to Biely et al. (1988). Native gels with fractionated proteins are layered over an agar-RBB-xylan gel preheated to 35–40° C. and incubated at room temperature until products are clearly visible. The agar layer is then removed from the separation gel and dipped into ethanol-0.05 M acetate buffer (2:1, pH 5.4). Xylanase activity is detected as an increase in the rate of diffusion of dyed fragments resulting from polysaccharide hydrolysis.

In a preferred embodiment of the invention, the plant promoter controllable by a phosphorus compound is operatively linked to a polypeptide coding region such as the one encoding Xylanase. In embodiments of the invention where recovery of an expressed coding region product is to be recovered, it is also preferred that the product be exuded by the plant material. For example, visualization of exuded Xylanase from roots is performed by growing transgenic plants on agar medium containing RBB-xylan. Tobacco seeds are germinated on the agar medium containing 2.5 mg/ml of RBB-xylan and the growth of roots is visually monitored for 30 days. Clear zones around the roots of transgenic plants form as a result of exuded Xylanase activity. Sethu et al, Phytochemistry 42: 961–966 (1996).

Quantification of exoxylanase activity is performed using the reducing sugar equivalent method described by Grepinet et al., J. Bacteriol. 170:4582–4588 (1988). In brief, root exudates of wild-type (control) and transgenic plants are heat-treated for 20 minutes at 65° C., and concentrated 10-fold by ultrafiltration. A 300 µl aliquot of each sample is added to 0.2 ml of 0.15% w/v xylan (Birchwood; Sigma Chemical Co.) prepared in 100 mM NaOAc (pH 5.4), and the mixture is incubated at 37° C. in a thermostatic shaker. After 30 minutes, the incubation reaction is stopped by rapid cooling to room temperature, followed by the addition of 0.6 ml of dinitrosalicylic reagent. Glucose is used to prepare standard curves. Duplicate control reactions are stopped prior to any incubation. Samples are boiled 10 minutes and the absorbance at 500 nm is determined spectrophotometrically. Enzyme activity is assayed using equivalent concentrations of xylose. One unit of Xylanase activity is defined as that quantity of enzyme that catalyzed the formation of 1 micromole of reducing group per minute (Achmed et al., Plant Physiol. 65: 1014–1016 (1980)).

Exudates produced by e.g., roots, leaves, etc. are used in methods according to the invention. Having been externalized by the plant or plant portion, exudates are readily obtained by any conventional method, including intermittent or continuous fluid bathing of the plant portion (whether isolated or part of an intact plant). Preferably, exudates are obtained by contacting the plant or plant portion with an aqueous solution such as a growth medium or water. The fluid-exudate admixture is then subjected to conventional polypeptide purification techniques to isolate the desired polypeptide. Of course, the invention contemplates recovery of coding region products by any method known in the art, including invasive/destructive techniques, isolation from secretions or exudations, and others.

EXAMPLE 7

Expression of SEAP using Transgenic Tobacco Plants

Transformation of tobacco plants (line SN-27) to introduce the human Secreted Alkaline Phosphatase (SEAP) coding region under the control of a phosphorus-controllable plant promoter is performed as described above. Transgenic tobacco plants transformed with the human secreted alkaline phosphatase (SEAP) gene under the control of the phosphorus-controllable plant promoter are also rooted and aseptically cultivated in liquid medium for 33 days. Transgenic plants are tested for the presence of specific mRNAs by Northern hybridization, using the method of Chomczynski et al., Anal. Biochem. 162:156 (1987) to isolate total RNA from leaf and root tissues. Transformed plants are expected to show expression of SEAP-specific MRNA. Plants transformed with the human SEAP gene under the control of a phosphorus-controllable plant promoter are expected to show similar mRNA expression levels in both leaf and root tissues.

In a preferred embodiment, the coding region product (i.e., SEAP), a recoverable polypeptide, is recovered from an exudate of an intact tobacco plant portion (i.e., roots). The recovery is accomplished as described above for Xylanase. SEAP activity is determined in liquid medium following 33 days of root growth and the removal of the roots to recover SEAP, as well as in the intercellular fluids. The chemiluminescent substrate CSPD, provided in the Great EscAPe SEAP Chemiluminescence Detection kit (Clontech, Inc.), is used to monitor the expression of SEAP by measuring secreted phosphatase activity. Chemiluminescent detection of SEAP activity is performed using either a Turner TD-20e Luminometer or by exposing the 96-well microtiter plates containing reaction products to X-ray film.

The assay is performed with 25 µl samples of either intercellular fluid or root exudates. The samples are placed into 75 pl of proprietary dilution buffer (Clontech, Inc.) and incubated for 30 minutes at 65° C. to inactivate endogenous phosphatase activity. Subsequently, samples are incubated for 10 minutes with CSPD and a chemiluminescence enhancer in a reaction buffer containing L-homoarginine as an inhibitor of endogenous phosphatases, as described by Cullen et al., Methods Enzymol. 216:362–368 (1992). Samples from untransformed tobacco plants provide negative controls; samples containing purified Placental Alkaline Phosphatase serve as positive controls.

Phosphatase activity is monitored in 50 individual tobacco plants transformed with the SEAP gene under the control of a phosphorus-controllable plant promoter. Transgenic plants are expected to show SEAP activity. No phosphatase activity is expected to be detected in wild-type plants.

Thus, a recombinantly expressed protein (SEAP) was recovered from the exudate of transgenic tobacco plants without injury to the plants or expensive and cumbersome purification protocols to isolate the desired product. Other embodiments of the invention either do not involve recovery of the expressed coding region product or involve other recovery techniques (e.g., vacuum infiltration, mechanical or chemical plant cell lysis) known in the art.

The invention contemplates methods including a wide variety of sexually or vegetatively propagated plants, as well as intact living plant portions such as excised leaves, stems, roots, flowers, etc. Preferred for use in the methods of the invention are plant species representing different plant families such as tobacco, tomato, rapeseed, alfalfa and turfgrass. Other preferred plants are aquatic plants capable of vegetative multiplication, such as Lemna and other duckweeds, Azolla, floating rice, water hyacinth, and the flowering plants that grow submerged in water, such as eelgrass and wilgeon grass.

The plant or plant portion which is subjected to the process of the present invention is a living plant or plant portion which is intact, and which is capable of being sustained without the use of organic nutritional supplements and without maintaining sterile conditions for the plant. However, sterile conditions or inorganic supplements may be employed in the methods of the invention.

The plant which is used in the present invention may be a mature plant, an immature plant such as a seedling, or a plant germinating from a seed. Seeds may be germinated in natural waters or germinated in prepared solutions or open fermenters. As noted above, a plant portion may also be used. Preferred plant portions are capable of being sustained without organic nutrient supplementation and do not require sterile conditions.

The plants, plant portions, or isolated plant cells for use in the methods of the invention may be genetically modified by, e.g., transformation with wild-type or recombinant *Agrobacterium tumefaciens*. In general, the plants or plant portions may exhibit a genotype that differs from the genotypes of any naturally existing plants. Moreover, the genetic modification may be achieved by any one of the conventional methods for altering the genetic content of cells, as is understood in the art. Typical genetic modifications would involve the introduction of a heterologous coding region.

One of ordinary skill in the art will also appreciate that the methods of the invention do not necessarily destroy the plants or plant portions. Accordingly, the methods may be either continuous or batch-mode processes.

EXAMPLE 8

Expression of GFP using Transgenic Tobacco Plants

Transformation of plants, hydroponic cultivation, and sample collection are performed as described in the preceding Examples. Transgenic GFP plants are tested for the presence of specific mRNAs by Northern hybridization. Total RNA is isolated from leaf and root tissues using the procedure of Chomczynski et al., (1987). All transformed plants are expected to express GFP-specific mRNA.

The unique bioluminescent features of GFP (excitation at 475 nm, emission at 510 nm) are used to microscopically detect and localize this protein in plant tissues and liquid samples. Plant roots freshly prepared in 0.05 M Tris-HCl, pH 8.0, are irradiated in the long-UV range of the electromagnetic spectrum with a fluorescent microscope (Nikon, Inc.). Transgenic roots are exposed to UV for an empirically optimized period of 30 seconds, which maximizes the distinction between the brightly fluorescing roots of transgenic plants and the non-fluorescing roots of wild-type plants.

To investigate the possibility of recovering secreted and exuded GFP, intercellular fluid and culture media are exposed to DEAE-Sephacel anion-exchange beads (Sigma Chemical Co.) to immobilize proteins. Anion-exchange beads incubated with the intercellular fluid or exudates of control plants are expected to be pale yellow under the fluorescent microscope, while beads exposed to the apoplastic fluid or root cultivation medium of GFP transformants should exhibit a bright green fluorescence, indicating the presence of secreted GFP. Other embodiments of the invention do not involve recovery of GFP, or recover the products using any of the methods known in the art.

Immunological detection of GFP is performed by Western blotting using anti-GFP monoclonal antibodies produced by mouse hybridoma cells (Clontech, Inc.) using, e.g., the Western Exposure Chemiluminescent Detection System PT 1600–1, available from the same supplier. Proteins isolated from the root exudates and root intercellular fluid are separated on 12% PAGE and electophoretically transferred onto PVDF membranes using the Bio-Rad Mini-Protein system (100 V constant voltage at 4° C., 1.5 hours). Prestained low-molecular weight SDS-PAGE standards (Bio-Rad Laboratories, Inc.) are used as molecular weight markers. Primary antibodies are diluted 1:500 and the secondary antibody-alkaline phosphatase conjugate is diluted 1:15,000. A single sharp band corresponding to a 27 kDa protein is expected for protein samples of root exudates and root intercellular fluid of transgenic plants. No specific detectable signals are anticipated for the corresponding samples of wild-type plants.

EXAMPLE 9

Expression of HbsAgS and HbsAgM using Transgenic Plants

Hepatitis B virus (HBV) is the human member of the hepadnaviradae family of viruses which infects over 300 million people worldwide. The HBV genome encodes three related envelope proteins, termed L, M, and S. The three proteins are produced from a single open reading frame through alternative translation start sites. All three proteins have a common N-linked glycosylation site specified by the S coding region, while the M protein alone contains an additional glycosylation site at amino acid position 4 of the pre-S2 domain. Recently, Mehta et al., Proc. Natl. Acad. Sci. (USA) 94:1822–1827 (1997), disclosed that glycosylation of the M protein is critical for its secretion from animal cells.

For the expression of hepatitis B surface antigen, the S-protein coding region and the M-protein coding region are translationally fused to a Calreticulin signal peptide coding region operably linked to a phosphorus-controllable plant promoter using, e.g., the materials and techniques described above. To facilitate cloning, DNA fragments encoding the S and M proteins are amplified by PCR using specific primers and pHB320 as a template, as described by Bichko et al., FEBS Lett. 185:208–212 (1985). This plasmid, pHB320, contains the complete genome of the ayw subtype of Hepatitis B.

Transformation and analysis of the transformed plants are performed as described above. Protein is recovered using any technique known in the art. In a preferred embodiment, protein exuded from the roots (i.e., root exudate) or leaves (i.e., guttation fluid exuded from hydathodes) of transgenic plants is analyzed using commercially available antibodies against HBV surface proteins.

EXAMPLE 10

Expression of Heterologous Polypeptides Using Transgenic Tomato Plants

Plasmids comprising polynucleotides according to the invention, such as the operable linkage of a phosphorus-controllable plant promoter to the coding region of either GFP or SEAP, are used to transform tomato plants (variety Dinasty). Tomato transformation is performed using a modification of the leaf-disk and *A. tumefaciens* co-cultivation protocol known in the art. The protocol is modified by using an *A. tumefaciens* titer of about $10^7$ cells/ml, the cells having been grown overnight in liquid LB medium. For nurse plates, MS salts are reduced to 10% of their normal concentration, as described by Weissbach et al., in Methods for Plant Molecular Biology (Weissbach and Weissbach, Eds., Academic Press, Inc. 1988), using a suspension culture of *N. tabacum* as the nurse culture. The *N. tabacum* cells are grown in liquid medium containing MS salts, $B_5$ vitamins, sucrose (30 g/L) and p-chlorophenoxyacetic acid (2 mg/L). Nurse plates are prepared by adding a 1.0–1.5 ml aliquot of the *N. tabacum* culture to the plate and covering the aliquot with an 8.5 cm disk of Whatman No. 1 filter paper. Infected plants are placed on top of the filter paper and incubated. Selection and regeneration of transformants are performed on a selective medium supplied with 25–50 mg/l of kanamycin.

Analysis of the transformed plants is performed as described above, and the heterologous polypeptides are recovered, if desired, using any technique known in the art.

EXAMPLE 11

Expression of Heterologous Polypeptides using Transgenic Turfgrass

Plasmids comprising polynucleotides according to the invention are used to construct a transformation vector for the expression of GFP in turfgrass, a monocot.

Transformation of turfgrass is carried out using a particle gun transformation method. See, Christou, Euphytica 85:13–27 (1995) and Johne et al., Euphytica 85:35–44 (1995). Analysis of the transformants and optional polypeptide recovery are accomplished as described above.

EXAMPLE 12

Expression and Recovery of Heterologous Polypeptides from Guttation Fluid using Transgenic Tomato Plants Plasmids comprising polynucleotides according to the invention are used to independently transform tomato plants (variety Dinasty), as described in Examples 2 and 7. Transformed tomato plants are grown in soil which is covered by a water-impermeable barrier. An opening in the barrier allows the stems of the tomato plants to extend above the soil. Water is supplied to the soil by any conventional technique for introducing water that is compatible with the water-impermeable barrier, e.g., water may be pumped into the soil using conventional piping or tubing. The leaf and stem portions of the tomato plants are contacted with an aqueous medium, which may be water, and the heterologous polypeptide is recovered in an admixture of aqueous medium and a plant exudate such as guttation fluid. The admixture may be collected from the surface of the water-impermeable barrier. The fluid is then subjected to conventional purification methodologies to recover the exuded polypeptide.

In accordance with another aspect of the invention, an aqueous medium contacting step is omitted and undiluted plant exudate, e.g. guttation fluid, is recovered. In one embodiment, guttation fluid is passively collected on a barrier due to gravitational force. In other embodiments, active collection of the exudate is accomplished by mechanical agitation of the plant or a portion thereof Mechanical agitation serves to induce exudate movement, in the ultimate direction of the barrier, for example by flowing down the plant or portion thereof or by traveling through the air in the form of drips or mist. The agitator may be any conventional means for inducing exudate movement. Examples include a rod or a cable for making sufficient contact with a plant or portion thereof to effect its physical deflection, resulting in movement of the exudate. Of course, the agitation may directly contact the exudate, which is in contact with the plant or portion thereof In addition to mechanical agitators, the invention contemplates non-mechanical agitators such as pressurized gas, e.g air, delivered from any conventional source such as an air compressor. In still other embodiments, the heterologous polypeptide-containing exudate is recovered using a device that function as both agitators and collectors. For example, a water-impermeable implement may be brought into contact with the plant or portion thereof, e.g., by dragging the device across the plant or portion thereof The contact is sufficient to induce exudate movement and the device collects exudate separated from the plant or portion thereof. Alternatively, absorbing or blotting devices (e.g., paper, cloth, etc.) are used to contact the plant or portion thereof bearing the heterologous polypeptide-containing exudate.

As noted above, any conventional technique for soil watering may be used in the methods of the invention, including the use of gravity- or pump-driven water supply piping or tubing. Alternatively, the soil may contain any of the irrigation systems known in the art. In addition, the invention contemplates reliance on capillary action in passively supplying water to the soil from adjacent areas. Those of skill in the art will recognize that, in addition to soil-based methods for recovering heterologous polypeptide from exudates, the methods of the invention may be practiced using other forms of plant culture, such as hydroponics and aeroponics.

The water-impermeable barrier may be any substance suitable for preventing the passage of aqueous solutions without adulterating those solutions by releasing chemical constituents of the barrier. Preferably, the barrier can withstand typical environmental conditions of temperature, wind, etc. Also preferred are flexible barriers that are readily molded to existing or engineered soil contours.

The soil may be left in its natural topography or re-shaped to suit the methods of the invention. For example, the soil may be shaped into a collection of hillocks which, in combination with a flexible barrier, maximizes recovery of exuded polypeptide by directing the aqueous fluid containing an exudate away from any opening in the barrier provided to allow passage of a plant stem.

While the present invention has been described in terms of specific embodiments, it is understood that variations and modifications will occur to those skilled in the art. Accordingly, only such limitations as appear in the appended claims should be placed upon the invention.

What is claimed is:

1. A method for expressing a coding region in a plant cell comprising the following steps:
   (a) transforming a plant cell with a polynucleotide comprising a plant promoter operably linked to a coding region; and
   (b) growing said cell under conditions such that said coding region is expressed,
      wherein said promoter comprises the sequence set forth in SEQ ID NO:1.

2. The method according to claim 1 wherein said coding region is heterologous to said plant cell and/or said promoter.

3. The method according to claim 1 further comprising contacting said plant cell with a regulatory compound, wherein said promoter is controlled by said compound.

4. The method according to claim 3, wherein said regulatory compound is selected from the group consisting of a phosphonus compound and a phosphorus-depriving agent.

5. The method according to claim 4 wherein said phosphorus-depriving agent is a monosaccharide.

6. The method according to claim 5 wherein said monosaccharide is mannose.

7. The method according to claim 1 wherein said promoter is obtained from a plant selected from the group consisting of *Arabidopsis thaliana* and Brassica species.

8. The method according to claim 1 wherein said polynucleotide is heterologous to said plant cell.

9. The method according to claim 1 wherein said plant cell is selected from the group consisting of *Arabidopsis thaliana*, *Nicotiana tabacum* and Brassica species.

10. An isolated polynucleotide comprising a plant promoter, wherein said polynucleotide comprises the sequence set forth in SEQ ID NO:1.

11. The isolated polynucleotide according to claim 10 wherein said promoter is operably linked to a heterologous coding region.

12. A vector comprising the polynucleotide according to claim 10.

13. A host cell comprising the polynucleotide according to claim 10.

14. A method for expressing a coding region in a plant cell comprising the following steps:
   (a) transforming a plant cell with a polynucleotide comprising a plant promoter operably linked to a coding region; and
   (b) growing said cell under conditions such that said coding region is expressed,
      wherein said promoter comprises a fragment of the sequence set forth in SEQ ID NO:1, and wherein said fragment retains phosphorus controllable promoter activity.

15. The method according to claim 14 wherein said coding region is heterologous to said plant cell and/or said promoter.

16. The method according to claim 14 further comprising contacting said plant cell with a regulatory compound, wherein said promoter is controlled by said compound.

17. The method according to claim 16 wherein said regulatory compound is selected from the group consisting of a phosphorus compound and a phosphorus-depriving agent.

18. The method according to claim 17 wherein said phosphorus-depriving agent is a monosaccharide.

19. The method according to claim 18 wherein said monosaccharide is mannose.

20. The method according to claim 14 wherein said promoter is obtained from a plant selected from the group consisting of *Arabidopsis thaliana* and Brassica species.

21. The method according to claim 14 wherein said polynucleotide is heterologous to said plant cell.

22. The method according to claim 14 wherein said plant cell is selected from the group consisting of *Arabidopsis thaliana, Nicotiana tabacum* and Brassica species.

23. An isolated polynucleotide comprising a plant promoter, wherein said polynucleotide comprises a fragment of the sequence set forth in SEQ ID NO:1, and wherein said fragment retains promoter activity.

24. The isolated polynucleotide of claim 23 wherein said promoter is operably linked to a heterologous coding region.

25. A vector comprising the polynucleotide according to claim 23.

26. A host cell comprising the polynucleotide according to claim 23.

* * * * *

UNITED STATES PATENT AND TRADEMARK OFFICE
CERTIFICATE OF CORRECTION

PATENT NO. : 6,544,789 B1
DATED : April 8, 2003
INVENTOR(S) : Raskin et al.

It is certified that error appears in the above-identified patent and that said Letters Patent is hereby corrected as shown below:

Column 29,
Line 53, please delete "phosphonus" and insert -- phosphorus -- therefor.

Column 30,
Line 52, please delete "phosphorus controllable".

Signed and Sealed this

Third Day of August, 2004

JON W. DUDAS
*Acting Director of the United States Patent and Trademark Office*